(12) United States Patent
Strongin et al.

(10) Patent No.: US 9,201,075 B2
(45) Date of Patent: Dec. 1, 2015

(54) COLORIMETRIC AND FLUOROMETRIC DETERMINATION OF HOMOCYSTEINE AND CYSTEINE

(75) Inventors: Robert M. Strongin, Baton Rouge, LA (US); Weihua Wang, Baton Rouge, LA (US); Oleksandr Rusin, Baton Rouge, LA (US); Nadia N. St. Luce, Hamilton, OH (US); Jorge O. Escobedo Cordova, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 977 days.

(21) Appl. No.: 11/587,507

(22) PCT Filed: Apr. 27, 2005

(86) PCT No.: PCT/US2005/014560
§ 371 (c)(1),
(2), (4) Date: Oct. 26, 2006

(87) PCT Pub. No.: WO2005/110109
PCT Pub. Date: Nov. 24, 2005

(65) Prior Publication Data
US 2008/0261315 A1 Oct. 23, 2008

Related U.S. Application Data

(60) Provisional application No. 60/651,480, filed on Apr. 30, 2004.

(51) Int. Cl.
*G01N 33/68* (2006.01)
*G01N 21/78* (2006.01)
(Continued)

(52) U.S. Cl.
CPC ............ *G01N 33/6815* (2013.01); *G01N 21/78* (2013.01); *G01N 33/52* (2013.01);
(Continued)

(58) Field of Classification Search
USPC .......................................................... 436/86
See application file for complete search history.

(56) References Cited

U.S. PATENT DOCUMENTS

| 5,885,767 A * | 3/1999 | Rozzell, Jr. ....................... 435/4 |
| 6,265,220 B1 | 7/2001 | Ullman ............................ 436/86 |

(Continued)

FOREIGN PATENT DOCUMENTS

| WO | WO 95/30151 | 11/1995 |
| WO | WO 01/33187 A2 * | 5/2001 |
| WO | WO 03/060478 | 7/2003 |

OTHER PUBLICATIONS

Rusin et al. ("Visual Detection of Cysteine and Homocysteine," J. Am. Chem. Soc. 2004, 126, 438-439, Published Online Dec. 19, 2003).*

(Continued)

*Primary Examiner* — Yelena G Gakh
*Assistant Examiner* — Michelle Adams
(74) *Attorney, Agent, or Firm* — John H. Runnels

(57) ABSTRACT

Colorimetric and fluorometric methods are disclosed for the rapid, accurate, selective, and inexpensive detection of homocysteine, or of homocysteine and cysteine, or of cysteine. The methods may be employed with materials that are readily available commercially. The novel methods are selective for homocysteine, for cysteine, or for total homocysteine and cysteine, and do not cross-react substantially with chemically-related species such as glutathione. The homocysteine-selective method does not have substantial cross-reactivity to the very closely related species cysteine. The cysteine-selective method does not have substantial cross-reactivity to the very closely related species homocysteine. The methods may be used, for example, in a direct assay of human blood plasma for homocysteine levels.

18 Claims, 18 Drawing Sheets

(51) Int. Cl.
*G01N 33/52* (2006.01)
*G01N 21/77* (2006.01)

(52) U.S. Cl.
CPC ...... *G01N2021/7769* (2013.01); *G01N 2021/7786* (2013.01); *Y10T 436/17* (2015.01); *Y10T 436/182* (2015.01)

(56) References Cited

U.S. PATENT DOCUMENTS

| | | | |
|---|---|---|---|
| 6,534,316 B2 | 3/2003 | Strongin et al. | 436/94 |
| 6,664,073 B1* | 12/2003 | Kawasaki et al. | 435/25 |
| 2005/0019937 A1 | 1/2005 | Shiue et al. | 436/86 |

OTHER PUBLICATIONS

Wang et al. ("Direct Detection of Homocysteine," J. Am. Chem. Soc. 2004, 126, 3400-3401, Published Online Mar. 2, 2004).*
"Putting color in homocysteine detection" in Science Concentrates, Chemical & Engineering News, 82 (Mar. 29, 2004) p. 24.*
Ohmori et al. ("A Simple and Specific Colorimetric Determination of Cysteine with p-Dimethylaminocinnamaldehyde," J. Clin. Chem. Clin. Biochem. 1983, 21, 851-857).*
Zhang et al. ("Thiazolidine Formation as a General and Site-Specific Conjugation Method for Synthetic Peptides and Proteins," Analytical Biochemistry 1996, 233, 87-93.).*
Wang et al., "Detection of Homocysteine and Cysteine," J. Am. Chem. Soc. 2005, 127, 15949-15958.*
Pacsial-Ong et al., "Electrochemical Detection of Glutathione Using Redox Indicators," Anal. Chem. 2006, 78, 7577-7581.*
Tanaka, F. et al. "Design and Use of Fluorogenic Aldehydes for Monitoring the Progress of Aldehyde Transformations," J. Am. Chem. Soc. 2004, 126, 3692-3693; published online Mar. 3, 2004.*
Tanaka, F. et al. "Determination of cysteine concentration by fluorescence increase: reaction of cysteine with a fluorogenic aldehyde," Chem. Commun. 2004, 1762-1763; published online Jun. 24, 2004.*
Wiebers, J. L. et al. "Homocysteine and Cysteine Synthetases of Neurospora crassa," J. Biol. Chem. 1967, 242, 12-23.*
Scifinder abstract of Tillian, H. M. et al. "Fluorodensitometric determination of cytostatically active Michael adducts of a,b-unsaturated aldehydes in biological material," Arzneimittel-Forschung, 35(2), 552-554 (1985).*

Inoue, T. et al., "Determination of thiols by capillary electrophoresis with amperometric detection at a coenzyme pyrroloquinone modified electrode," *Anal. Chem.*, vol. 74, pp. 1349-1354 (2002).
Nekrassova, O. et al., "Analytical Determination of Homocysteine: A Review," *Talanta*, vol. 60, pp. 1085-1095 (2003).
O'Shea, T. et al., "Selective detection of free thiols by capillary electrophoresis—Electrochemistry using a gold / mercury amalgam microelectrode," *Anal. Chem.*, vol. 65, pp. 247-250 (1993).
Refsum, H. et al., "Facts and recommendations about total homocysteine determinations: An expert opinion," *Clin. Chem.*, vol. 50, pp. 3-32 (2004).
St. Luce, N., "Optical Detection of L-Cysteine and L-Homocysteine via a Fluorescein Derivative," Chapter 5, pp. 59-79, in *Synthesis, Characterization and Study of Novel Reagents for the Detection of Saccharides and Amino Acids*, PhD Dissertation, Louisiana State University (Baton Rouge, Louisiana, 2004).
White, P. et al., "Electrochemically initiated 1,4 additions: A versatile route to the determination of thiols," *Analytica Chimica Acta*, vol. 447, pp. 1-10 (2001).
Zhao, R. et al., "Kinetics of one-electron oxidation of thiols and hydrogen abstraction by thiyl radicals from $\alpha$-amino C—H bonds," *J. Am. Chem. Soc.*, vol. 116, pp. 12010-12015 (1994).
Zhao, R. et al., "Significance of the intramolecular transformation of glutathione thiyl radicals to $\alpha$-aminoalkyl radicals. Thermochemical and biological implications," *J. Chem. Soc., Perkins Trans.*, vol. 2, pp. 569-574 (1997).
T. Nauser et al., "Thiyl radicals abstract hydrogen atoms from the $\alpha$C—H bonds in model peptides: absolute rate constants and effect of amino acid structure," *J. Am. Chem. Soc.*, vol. 125, pp. 2042-2043 (2003).
Zhang, X. et al., "One- and Two-Photon Turn-on Fluorescent Probe for Cysteine and Homosysteine with Large Emission Shift," *Org. Letters*, vol. 11, No. 6, pp. 1257-1260 (2009).
Lee, K-S et al., "Fluorescence Turn-On Probe for Homocysteine and Cystine in Water," *Chem. Commun.*, pp. 6173-6175 (2008).
Kim, Tae-Ki et al., "Highly Selective Fluorescent Sensor for Homocysteine and Cysteine," *Tetrahedron Letters*, vol. 49, pp. 4879-4881 (2008).
Lin, W. et al., "A Ratiometric Fluorescent Probe for Cysteine and Homocysteine Displaying a Large Emission Shift," *Org Letters*, vol. 10, No. 24, pp. 5577-5580 (2008).
Wang, D. et al., "Exploring the pH Dependence of Viologen Reduction by $\alpha$-Carbon Radicals Derived from Hcy and Cys," *Chem. Commun.*, pp. 1876-1878 (2009).

* cited by examiner

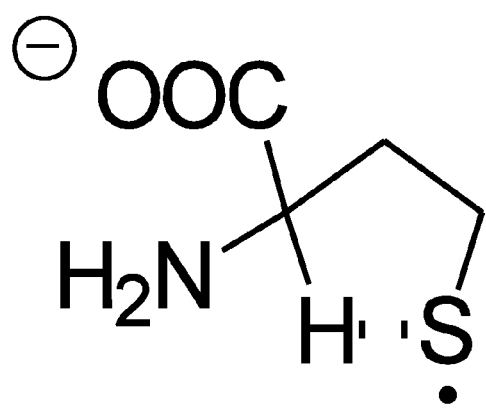
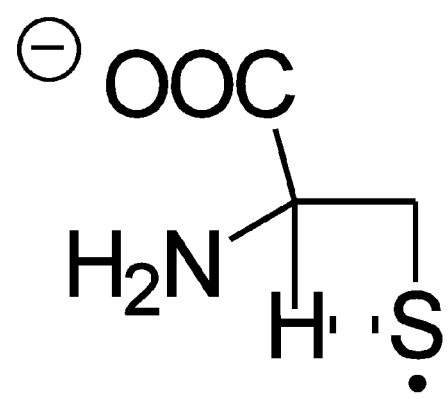
Prior Art
Prior Art
Fig. 1(a)
Fig. 1(b)

COLORIMETRIC AND FLUOROMETRIC DETERMINATION OF HOMOCYSTEINE AND CYSTEINE

This is the United States national stage of international application PCT/US2005/014560, filed Apr. 27, 2005; which claims the benefit of the Apr. 30, 2004 filing date of provisional application No. 60/651,480 under 35 U.S.C. §119(e).

The development of this invention was partially funded by the Government under grants R01EB002044 and R01GM61915 awarded by the National Institutes of Health. The Government has certain rights in this invention.

TECHNICAL FIELD

This invention pertains to the colorimetric and fluorometric determination of homocysteine, of cysteine, or of both homocysteine and cysteine.

BACKGROUND ART

The detection of biologically important thiols such as cysteine and homocysteine has been the focus of much research. Most reported methods have been based upon nonspecific redox chemistry, immunoassays, or upon derivatization with chromophores or fluorophores.

There is an unfilled need for a simple, rapid, accurate, and inexpensive method to assay homocysteine, including, but not limited to, homocysteine in plasma. There is an unfilled need for a simple, rapid, accurate, and inexpensive method to assay cysteine, including, but not limited to, cysteine in plasma. Ideally, such methods would employ stable, non-toxic reagents that afford high sensitivity and selectivity.

At elevated levels in plasma, homocysteine (Hcy) is a risk factor for Alzheimer's and cardiovascular diseases. Current methods for the direct detection of Hcy suffer from interferences caused by other common thiols, such as cysteine (Cys) and glutathione (GSH). Hcy analyses have thus typically been based on chromatographic separations or immunoassays. While such methods can be effective, it would be beneficial to have a simple, rapid method for assaying homocysteine, one that does not require the use of chromatographic or immunological techniques.

Cysteine deficiency has been implicated in conditions including slowed growth, hair depigmentation, edema, lethargy, liver damage, muscle and fat loss, skin lesions, and weakness. Again, interferences from other thiols are a concern. While there are a number of dyes that will react with thiols generally, with a resulting change in color, to the inventors' knowledge there have been no prior reports that any dye would react selectively with Cys or Hcy, or with both Cys and Hcy selectively over other thiols. It is believed that the present invention represents the first example of selective reaction with Cys or Hcy, or with both Cys and Hcy selectively over other thiols. The determination of specific thiols has often been carried out in conjunction with HPLC or capillary electrophoresis separations or via immunoassays.

Hcy has been reported to inhibit the oxidation of luminol and dihydrorhodamine by strong oxidants. Hcy also rapidly reduces ferrylmyoglobin to metmyoglobin. In one study of the ability of GSH, Cys, and Hcy to reduce dehydroascorbic acid (DHA), Hcy caused substantially greater reduction of DHA than did either Cys or GSH. Furthermore, Hcy can cause such reduction at Hcy concentrations more than an order of magnitude lower than those required for GSH and Cys. Hcy thus functions as a potent reducing agent in biological systems, although it may also be responsible for oxidative stress.

Biological thiols are characterized by a delicate balance between their oxidizing and reducing functions. Oxidizing thiyl radicals will rapidly equilibrate to reducing, captodative α-amino carbon-centered radicals under physiological, aerobic conditions. Additionally, reducing disulfide radical anions rapidly decay to the reducing α-aminoalkyl radicals. The equilibria in the free radical chemistry of biological thiols are pH-dependent, and include several radical and recombinant species.

Different naturally-occurring thiols, which may have similar structures, may have quite different physiological properties. The physiological effects and correlations that have been observed for these thiols are a public health concern. An improved ability to detect and quantitate low molecular weight biological thiols would be of great importance to diagnosing and understanding disease states.

Examples of low molecular weight thiols that have more-or-less similar structures, but that have disparate physiological properties, include cysteine, homocysteine, glutathione, N-acetylcysteine, and penicillamine. Generic methods for detecting thiols do not readily distinguish among such similar species. There is a substantial need for improved methods for detecting and quantitating biological thiols.

Thiols are easily oxidized. Many have similar structures. They are typically colorless and non-fluorescent at visible wavelengths. Current detection methods are often tedious. One current method is based on making derivatives with chromophores or fluorophores; but the products can be unstable, and the derivatization reactions often produce interfering byproducts. The relatively large excess of glutathione that is typically present in millimolar concentrations in biological media complicates the detection of other thiols.

The universal methylating agent S-adenosylmethionine (SAM) is synthesized from methionine and ATP. SAM is essential for one-carbon metabolism. Methylation via SAM produces S-adenosyl homocysteine (SAH). This reaction is followed by the enzymatic hydrolysis of SAH by S-adenosyl homocysteine hydroxylase (SAHH) to yield adenosine and Hcy. A trans-sulfuration pathway leading from Hcy to Cys commences at this point. Hcy reacts with serine via cystathionine-β-synthase (CBS), a vitamin $B_6$-dependent enzyme, to produce cystathionine. Cystathionine then reacts to form cysteine, a source of glutathione, sulfate, and sulfite.

But the synthesis of cystathionine is not the only potential fate of Hcy. Homocysteine can also be methylated, released into the extracellular medium, or deaminated. Hcy methylation to methionine can be carried out by methionine synthase in a folate-dependent manner, or via betaine homocysteine methylase.

When Hcy metabolism is disrupted, the export of Hcy from within cells to the extracelluar medium becomes imbalanced, and hyperhomocysteinemia can result. At lower Hcy levels, export rates to plasma and urine are elevated. Higher Hcy levels in plasma and urine are directly related to lower methionine synthase activity, and to folate or vitamin $B_{12}$ deficiency. "Hyperhomocysteinemia" is often defined as a condition in which plasma Hcy concentration exceeds 14 µM. It has been proposed that vitamin or folate therapy may be useful in treating hyperhomocysteinemia-related disorders.

In blood or plasma, Hcy may bind to other molecules. Approximately 99% of Hcy in plasma binds via disulfide linkages to proteins, other Hcy molecules, or other thiols. Oxidation to a disulfide in plasma is coupled to $O_2$ reduction, leading to oxidative stress. Reactive oxygen species (ROS)

levels can be diminished by peroxidases. However, hyperhomocysteinemia appears to inhibit the expression of peroxidases.

Nitric oxide (NO) released by endothelial cells can react with Hcy to produce S-nitrosohomocysteine (SNOHO), a strong antiplatelet and vasodilator agent. A consequence of nitrosylation is to repress peroxide production, and thereby to inhibit ROS formation. However, Hcy is not effectively deactivated by this mechanism at Hcy levels typical of hyperhomocysteinemia.

Low-density lipoprotein oxidized by ROS suppresses endothelial nitric oxide synthase expression. Hcy is believed to lower NO availability upon its own nitrosylation. NO is a neurotransmitter that is involved in muscle relaxation and microphage cytotoxicity. Lowered NO availability may be among the physiological effects of hyperhomocysteinemia. More importantly, Hcy impairs endothelial cell function in the absence of NO. Although the mechanism is not well understood, it is believed that the direct action of homocysteine on endothelial cells could either involve enhanced oxidative stress, or it could result from the direct effect of the oxidation products of homocysteine.

The impairment of endothelial cells by hyperhomocysteinemia is believed to be one cause of cardiovascular disease. It is believed that Hcy can switch the phenotype of endothelial cells from anticoagulant to procoagulant. In fact, homocysteine-mediated cardiovascular risk may be as high as the risk from hyperlipidemia. High homocysteine levels have been detected in up to 20% of people suffering from heart disease.

It is also known that the impairment of endothelial cells can result in the vasomotor dysregulation that causes Raynaud's syndrome. A recent study has shown the presence of elevated plasma homocysteine levels in Raynaud's syndrome patients.

Oxidative stress generated by hyperhomocysteinemia may be associated with brain damage and diseases such as Alzheimer's. Recent studies suggest that glutathione peroxidases are overexpressed in Alzheimer patients, linking the disease to oxidative stress in the brain. Elevated levels of plasma homocysteine have also been detected. Conversely, antioxidant supplements have been reported to delay the onset of Alzheimer's-related complications. An increased incidence of birth defects, and renal failure are among other diseases that have also been linked to hyperhomocysteinemia.

If hyperhomocysteinemia can be promptly and properly diagnosed, then the physiological effects of hyperhomocysteinemia may sometimes be reversed, at least in part. Proper diagnosis may help to prevent neural tube defects in pregnancy, ischemic heart disease, stroke, and possibly colon cancer. It has been reported that the risk of heart disease can be reduced by up to 40%. Folic acid supplementation has been recommended for these and related conditions.

For a recent review, see generally H. Refsum et al., "Facts and recommendations about total homocysteine determinations: An expert opinion," *Clin. Chem.*, vol. 50, pp. 3-32 (2004).

Cysteine is the final product of the trans-sulfuration pathway through homocysteine metabolism. The low water solubility of the disulfide reduces its excretion. It can therefore accumulate in urine (leading to cystinuria), or in various organs of the body (e.g., kidney stones). Low levels of cysteine have been associated with slowed growth, hair depigmentation, edema, lethargy, liver damage, muscle and fat loss, skin lesions, and general weakness.

To the knowledge of the inventors, there are no known prior direct colorimetric or fluorometric methods for the specific detection of biological thiols such as homocysteine or cysteine. Detection methods that have been used for these thiols have included chromatographic separations, immunoassays, enzymatic assays, electrochemical separation and detection, mass spectrometry, and flow injection techniques. Many of these prior detection methods have substantial inherent limitations.

Electrochemical detection is complicated by interference from oxidizable impurities. Electrochemical detection of thiols by capillary electrophoresis (CE) is hampered by the need for precision electrode alignment and isolation of the detector from the separation voltage. Amperometric post-column detection of cysteine and homocysteine also can suffer from low selectivity and high background current, as cysteine exhibits irreversible oxidation requiring a positive overpotential. The small volumes of the separation capillaries used in CE require that the detector be placed in-line to minimize line-broadening. Good sensitivity often requires dual electrode configurations. The stability of the detection cell components can be another concern. Mercury and mercury amalgam electrodes have been used for thiols, but their use is limited due to concerns that include toxicity and poor stability. Chemically modified electrodes require a complex preparation procedure, can exhibit poor stability, and need controlled working conditions.

Fluorescence polarization immunoassays (FPIA) and enzyme immunoassays (EIA) have shown (inter-laboratory) imprecision. FPIA requires long run times and has a low throughput. Enzymes are relatively unstable and expensive, making enzyme-based assays less attractive in spite of their potential for high specificity. Radioimmunoassays are undesirable due to the use of radioactive materials. STE (Substrate-Trapping-Enzyme) technology requires a batch chromatography step and has low precision.

Mass spectrometry (MS) coupled to high performance liquid chromatography (HPLC) requires complex, expensive equipment. Gas chromatography-mass spectrometry (GC-MS) also employs complex equipment, and requires tedious procedures that are not well-suited for routine diagnostic applications. Gas chromatography-electron capture detection and flame photometry detection require tedious sample preparations or high operating temperatures. Trap and Release Membrane Introduction Mass Spectrometry (T&R MIMS) requires time-consuming derivatizations and sophisticated instrumentation, making it not well-suited for routine analyses.

Derivatization of thiols with chromophores and fluorophores has also been used to determine specific thiols, often in conjunction with HPLC separations. Thiol derivatizing agents often contain electrophilic alkylating groups for reaction with sulfhydryl moieties. These agents include iodoacetamides, maleimides, and monobromobimanes (mBrB). These agents are typically non-selective among different thiols, and instead react with thiols generally, as well as other biomolecules. Interferences are therefore a concern. For instance, iodoacetamides will react with histidine, tyrosine, or methionine. Other reagents such as 1,1'-thiocarbonyl diimidazole will derivatize cysteine or penicillamine. Derivatization conditions are often time-consuming and complex, and they can sometimes lead to other problems. Excess derivatization agents must often be removed from the reaction mixture. In some cases, the derivatives are prone to unwanted further reactions. For instance, the products of isothiocyanates and succinimidyl esters with biological thiols have limited stability and undergo further reactions with amines to produce thioureas. Amines have been reported to crosslink the derivatized products of maleimide-based agents. Some thiol-chromophore/fluorophore derivatives are sensitive to light or to hydrolysis. The OPA-Hcy adduct is stable only in dark. On the other hand, mBrB produces fluorescent hydrolysis products. When thiols are derivatized with certain maleimides, hydrolysis peaks are seen at both the beginning and the end of chromatographic elution. Hexaiodoplatinate, on the other hand, produces no hydrolysis products. However, hexaiodoplatinate exhibits a broad reactivity; thioethers, thiazolidines and ascorbic acids are among the reported interferences.

Some derivatization agents themselves are prone to instability. Iodoacetamides are unstable to light. In addition, mBrB is photosensitive, and is unstable in water. The instability of certain maleimides in aqueous conditions necessitates the use of water-miscible organic co-solvents.

Commercially available thiol and sulfide quantitation kits use an enzymatic reaction to release thiols, followed by their determination with Ellman's reagent. However, enzymes are expensive and fragile.

Methylviologen ($MV^{2+}$) is the ammonium dication:

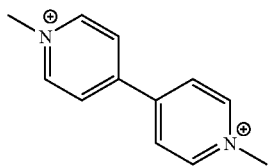

$MV^{2+}$ has been used as an oxidant in an investigation of the equilibrium kinetics of both the reducing disulfide and the α-amino carbon-centered radicals derived from Hcy, Cys and GSH. Reducing radical formation was monitored via changes in the UV-Vis spectra of solutions containing the methylviologen radical cation that formed in the presence of the biological thiols. See R. Zhao et al., "Kinetics of one-electron oxidation of thiols and hydrogen abstraction by thiyl radicals from α-amino C—H bonds," *J. Am. Chem. Soc.*, vol. 116, pp. 12010-12015 (1994); and R. Zhao et al., "Significance of the intramolecular transformation of glutathione thiyl radicals to α-aminoalkyl radicals. Thermochemical and biological implications," *J. Chem. Soc., Perkins Trans.*, vol. 2, pp. 569-574 (1997) It was surmised that formation of the reducing α-aminoalkyl radical derived from Hcy should be particularly favorable, due to an intramolecular hydrogen abstraction mechanism involving a five-atom ring transition state (See FIG. 1(*a*)). By contrast, in the case of either Cys or GSH, H-atom abstraction to a reducing carbon-centered radical would proceed via less-favored four-membered ring (FIG. 1(*b*)) or nine-membered ring (not shown) transition state geometries, respectively. See FIGS. 1(*a*) and 1(*b*), depicting the inferred proton abstraction leading to formation of the α-aminoalkyl radical from the thiyl radicals of Hcy and Cys, respectively. These references did not describe any appreciable colorimetric selectively among homocysteine, cysteine, and glutathione.

Zhao et al. (1994) and Zhao et al. (1997) both describe procedures conducted in the absence of atmospheric oxygen. For example, Zhao et al. (1997) at page 570 states: "The solutions were deoxygenated by bubbling with Ar gas, and subsequently saturated with $N_2O$, Since oxygen was suspected to be critical, the purging gas was bubbled through an alkaline pyrogallol solution to reduce the oxygen level as much as possible."

T. Inoue et al., "Determination of thiols by capillary electrophoresis with amperometric detection at a coenzyme pyrroloquinone modified electrode," *Anal. Chem.*, vol. 74, pp. 1349-1354 (2002) describes the use of a chemically-modified electrode to detect and determine thiol-containing compounds following capillary electrophoresis separation. The solutions used in the analysis were deoxygenated with either an argon purge or a nitrogen purge.

P. White et al., "Electrochemically initiated 1,4 additions: A versatile route to the determination of thiols," *Analytica Chimica Acta*, vol. 447, pp. 1-10 (2001) discloses the electrochemical generation of quinoid intermediates and their subsequent reaction with sulfhydryl thiols as a method for quantifying thiols. The solutions used were degassed and stored under argon. All solutions were generally used within one hour of preparation to minimize losses from aerial oxidation.

T. O'Shea et al., "Selective detection of free thiols by capillary electrophoresis—Electrochemistry using a gold/mercury amalgam microelectrode," *Anal. Chem.*, vol. 65, pp. 247-250 (1993) discloses a method for the detection of thiols by the catalytic oxidation of mercury in the presence of thiols. Deoxygenation was said to be important for reproducibility of the response. The buffer reservoirs were deoxygenated by sparging with argon.

Colorimetric and fluorometric methods for the analysis of carbohydrates are disclosed in U.S. Pat. No. 6,534,316.

A review of current methods for determining homocysteine is given in O. Nekrassova et al., "Analytical Determination of Homocysteine: A Review," *Talanta*, vol. 60, pp. 1085-1095 (2003). The drawbacks of current techniques are highlighted in this review. At page 1093 the authors acknowledged that "to date the reaction protocol has not been developed for the selective determination of homocysteine . . . . " At page 1094 the authors concluded that the existing "techniques have been shown to produce various advantages in terms of sensitivity depending on the conditions required, however, the lack of selectivity inherent in so many of the procedures means that there is always the need for a separation technique to be utilised before detection can occur. This often can add expense and delay in the sample analysis, but has the advantage of producing both a selective and sensitive detection process. Therefore, the ultimate aim would be to produce a device capable of producing both a sensitive and selective analysis with minimal sample pre-treatment and ability to quantitate 1 µM differences."

There remains an unfilled need for improved, simple methods for determining homocysteine and cysteine.

The present invention has successfully achieved what the authors of the Nekrassova et al. article characterized as "the ultimate aim" in this field. The present invention is based on a simple calorimetric assay. Qualitatively, the assay may be conducted without any instruments at all, relying just upon a visual inspection of color. If quantitative results are desired, they may be obtained, for example, with instrumentation that need be no more complex than an ordinary absorbance or fluorescence spectrometer.

DISCLOSURE OF INVENTION

We have discovered calorimetric and fluorometric methods for the rapid, accurate, selective, and inexpensive detection of homocysteine, cysteine, or homocysteine and cysteine. The methods may be employed with materials that are readily available commercially. The novel methods are selective for homocysteine, for cysteine, or for total homocysteine and cysteine, and do not cross-react substantially with chemically-related species such as glutathione. The homocysteine-selective method does not have substantial cross-reactivity to the very closely related species cysteine. The cysteine-selective method does not have substantial cross-reactivity to the very closely related species homocysteine. The novel methods have been successfully used, for example, to assay homocysteine levels in human blood plasma directly.

Unlike prior (less specific) methods for detecting thiols, the present invention does not require anaerobic conditions to function; the methods disclosed here were all observed to function properly in an ordinary atmosphere containing oxygen.

BRIEF DESCRIPTIONS OF THE DRAWINGS

FIGS. 1(a) and 1(b) depict the inferred proton abstraction leading to formation of an α-aminoalkyl radical from the thiyl radicals of Hcy and Cys, respectively.

Figure 10A:
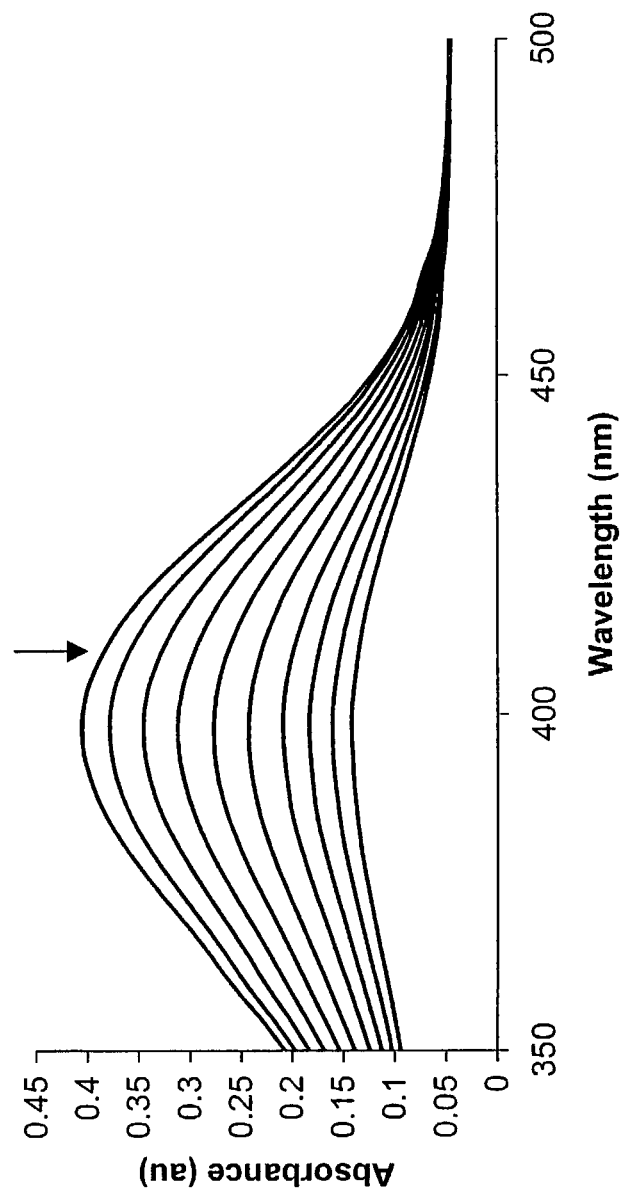

FIGS. 10(a) and (b) depict UV/Vis absorption spectra of solutions of 4-(dimethylamino) cinnamaldehyde at various concentrations of added L-cysteine or added homocysteine, respectively.

Figure 11A:
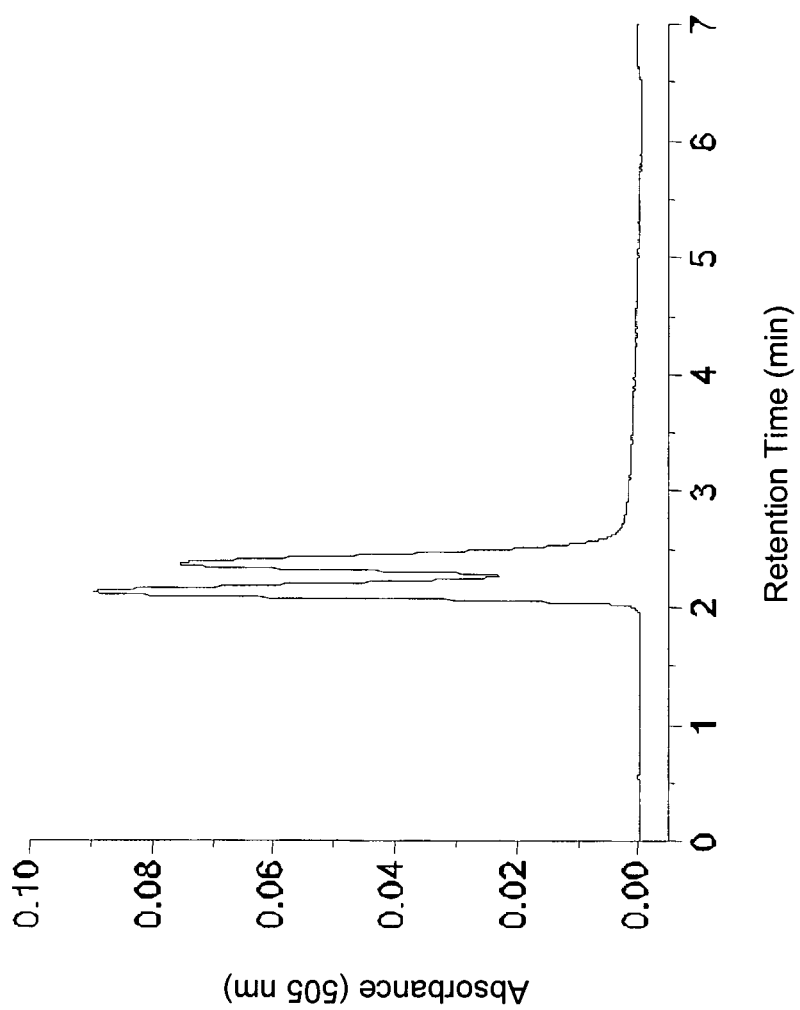
Figure 11B:
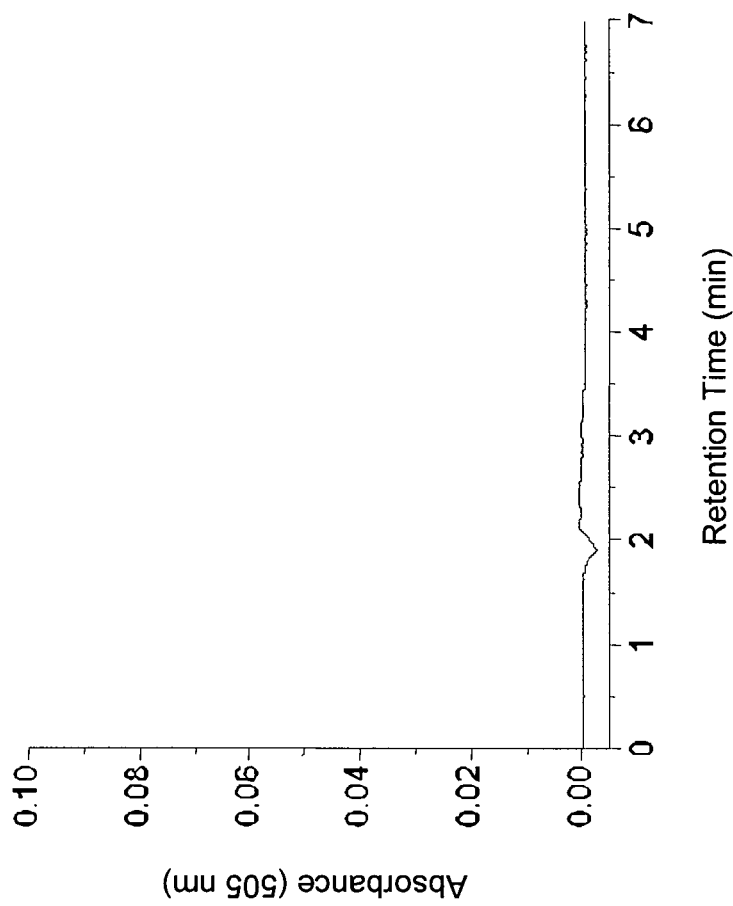
Figure 11C:
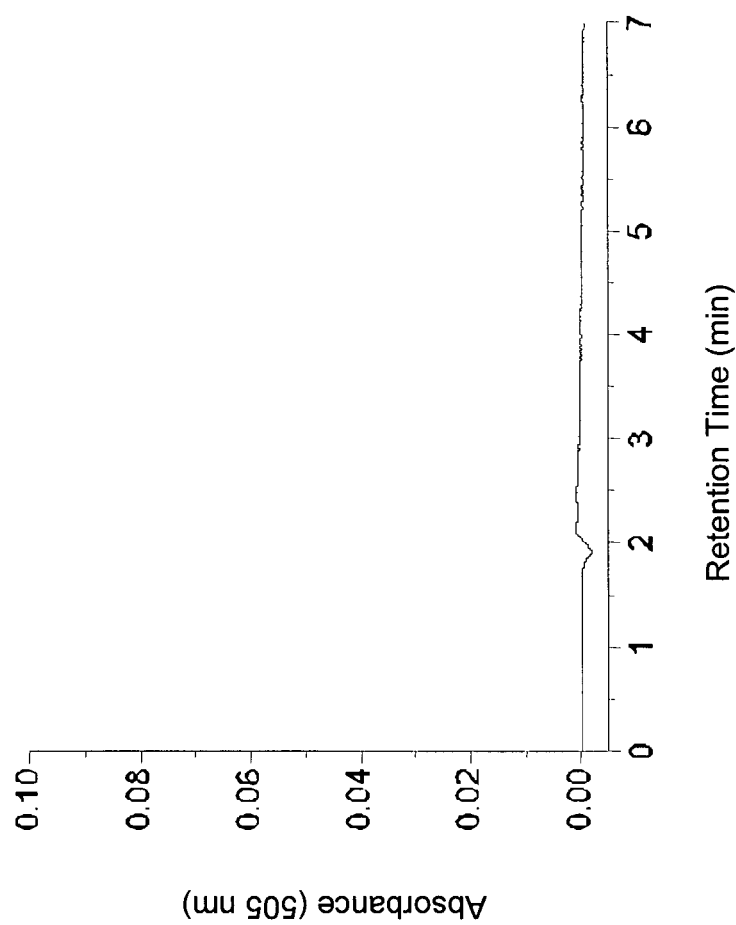
Figure 11D:
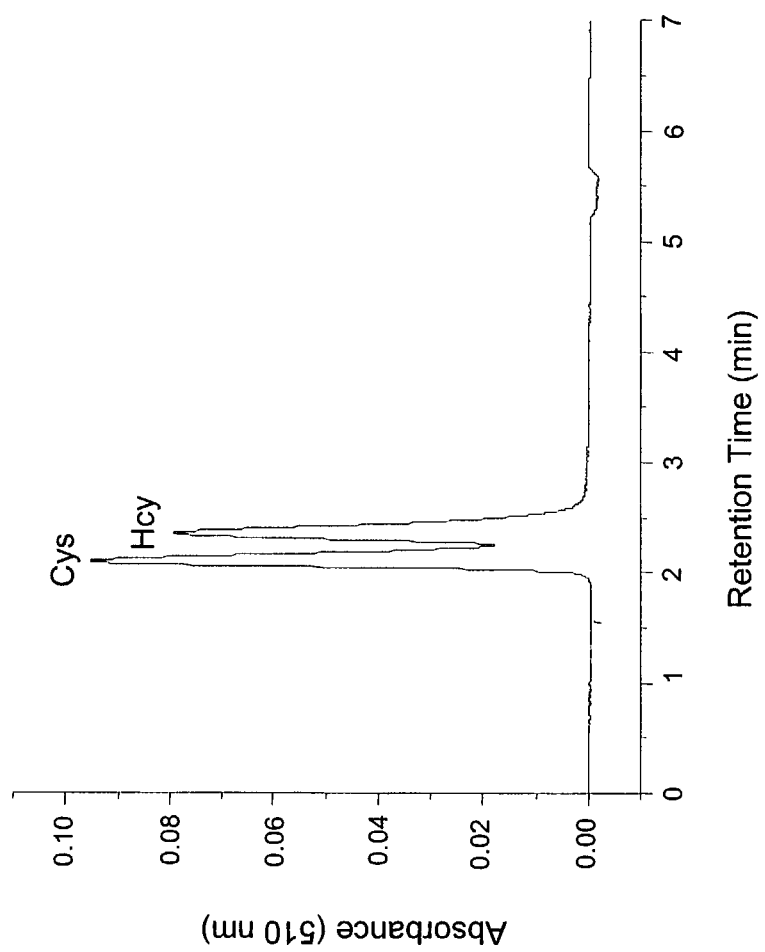
Figure 11E:
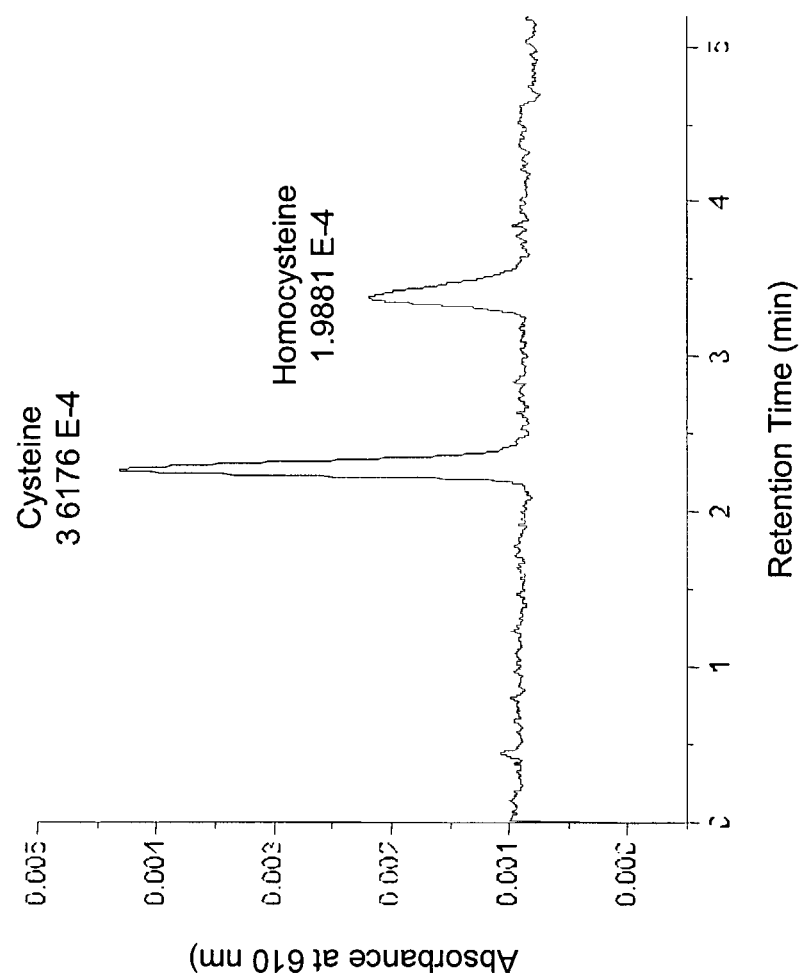

FIG. 11(a) depicts an HPLC plot for cysteine and homocysteine, using fluorone black as a post-column detection reagent. FIGS. 11(b) and 11(c) depict HPLC plots for the amino acids histidine, methionine, and glutamine; and for the amino acids lysine, glycine, and serine, respectively, using fluorone black as a post-column detection reagent. FIG. 11(d) depicts an HPLC plot for cysteine and homocysteine, using fluorescein dialdehyde as a post-column detection reagent. FIG. 11(e) depicts an HPLC plot for cysteine and homocysteine, using methyl viologen as a post-column detection reagent.

Figure 12:
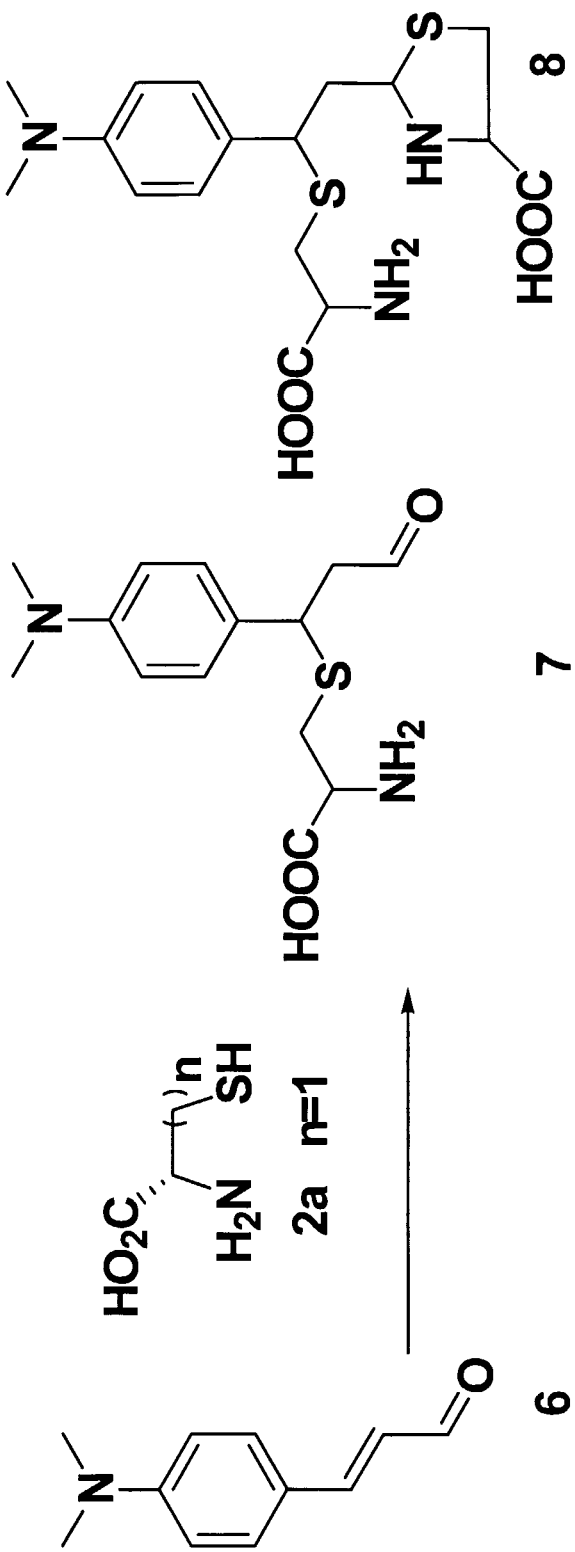

FIG. 12 depicts the reaction of Compound 6 with cysteine to form the colorless products Compounds 7 and 8.

Figure 13:
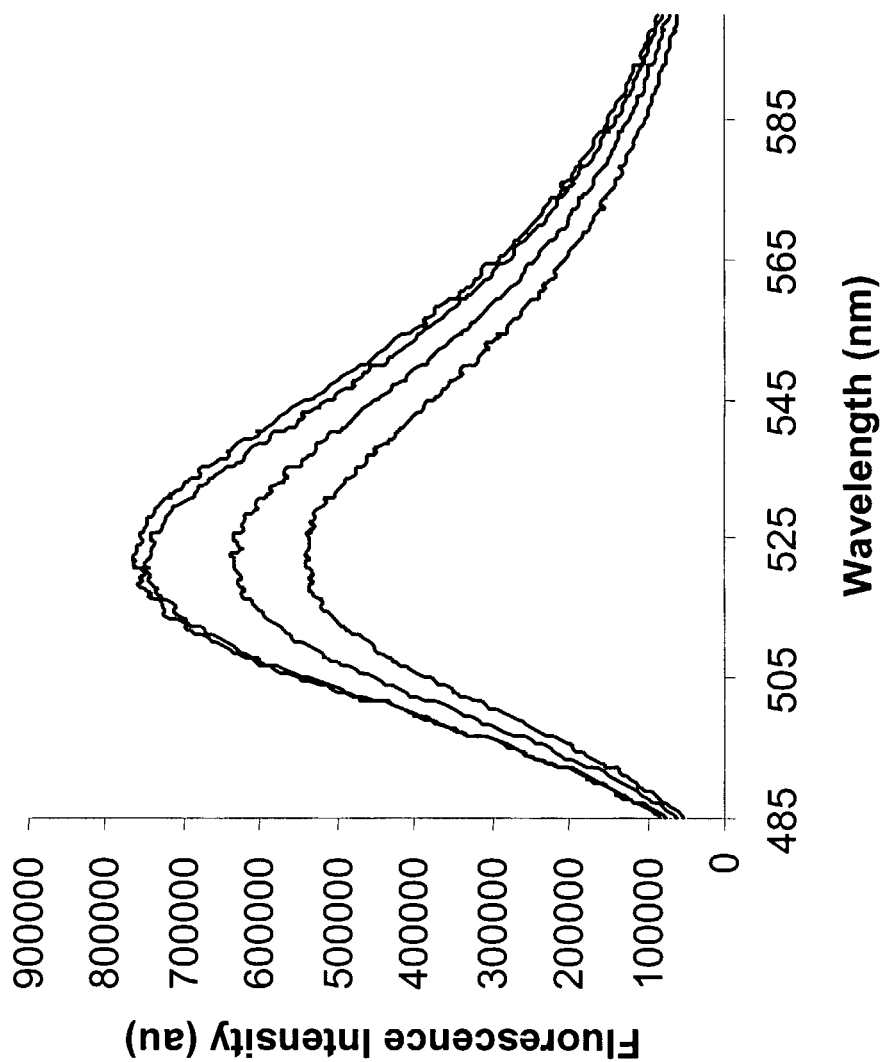

FIG. 13 depicts fluorescence emission spectra of different analytes with a mixture of two aldehydes in deproteinized blood plasma.

MODES FOR CARRYING OUT THE INVENTION

Determination of Homocysteine

The specific determination of homocysteine is preferably conducted at or near neutral pH with gentle heating. A solution of methylviologen (or other suitable indicator, as discussed further below) changes color selectively in the presence of Hcy upon gentle heating at or near neutral pH. Alternatively, in solutions containing fluorone black (Compound 4) and a reducing agent, such as a phosphine such as $PPh_3$, Hcy may be selectively detected at room temperature by visible, near-infrared, or ultraviolet absorbance or fluorescence spectroscopy.

Gentle heating and near-neutral pH are important for the selective reaction of $MV^{2+}$ with Hcy. The temperature should be between about 25° C. and about 110° C., i.e., a temperature conducive to such a selective reaction, preferably about 50° C., for about 5 minutes or longer. (The reaction time depends on temperature, and will generally be shorter at higher temperatures.) The pH should be in a range between about 3.9 and about 9.5, preferably between about 6 and about 8, most preferably about 7.5.

The novel method allows detection of Hcy under ambient conditions, circumstances where direct bioassays might have been used in the past. As compared to bioassays, however, the novel method is simpler, less expensive, and easier to quantitate.

Example 1

For example, upon heating a sample with a colorless solution of $MV^{2+}$ (e.g., 4.0 mM) at a very gentle reflux (e.g., 5 min, pH 7.5, 0.1 M Tris buffer in $H_2O$, 17 mM Hcy), a visual signal that was selective for Hcy was clearly seen. To the unaided eye, a sample containing 17 mM Hcy turned blue; while a control with a blank sample, a sample with 17 mM Cys, and a sample with 17 mM GSH all remained colorless. Spectroscopically, the color formation can be monitored via the appearance of absorption peaks at 398 nm and at 605 nm.

Example 2

Surprisingly, the color change induced in methylviologen by homocysteine was found to be reversible, simply by varying the temperature. In experiments conducted as otherwise described in Example 1, at temperatures higher than about 40° C. the formation of color was stable, but when the temperature was decreased (below about 40° C.), the color faded in less than a minute. This cycle could be repeated many times: increasing temperature restored the color, and decreasing it caused the color to fade.

The reversibility of the reaction may be useful, for example, in continuous Hcy monitoring, recycling the sensor material, or both, thereby reducing cost.

Example 3

Figure 2:
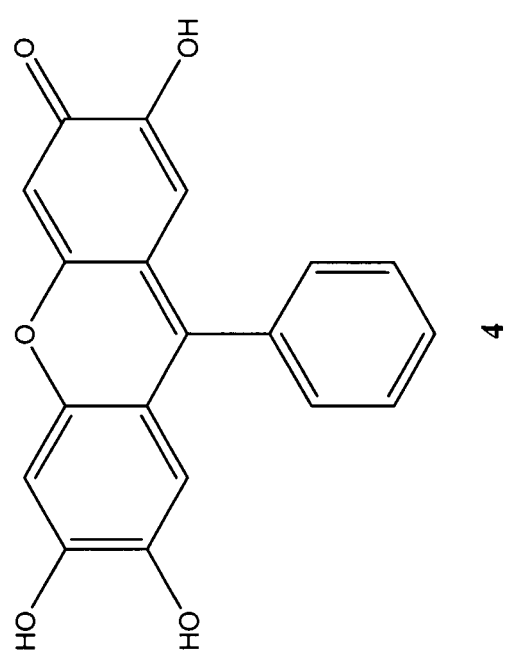
FIG. 2 depicts the structure of the compound fluorone black (Compound 4).

An alternative method for the selective detection of homocysteine employs fluorone black, Compound 4. (See FIG. 2.) Following the addition of a thiol (Hcy, Cys, or GSH) to a solution of Compound 4 ($1.0 \times 10^{-5}$ M) in 70% MeOH/$H_2O$ (phosphate buffer, $H_2O$, pH=7.3), an increase in absorbance occurred at 510 nm at room temperature (analysis after 5 min). The absorbance increase was greatest for Hcy as compared to equimolar amounts of the other two biothiol analytes. Amino acids lacking thiol functionality, such as L-alanine, L-arginine, L-glutamine, glycine, L-lysine, L-methionine, L-serine, and L-threonine, did not produce substantial spectral changes at 510 nm as compared to solutions of Compound 4 without analyte. Note in particular that methionine, which contains a sulfur atom but not a thiol group, did not produce a substantial spectral change at 510 nm.

We have discovered that potential interferences may be minimized, and outstanding selectivity achieved, by the addition of a reducing agent such as a phosphine derivative (5 equiv. to analyte in this example).

Without wishing to be bound by this theory, our findings suggested a process in which Compound 4 was involved in the redox chemistry of the thiols. $^1$H NMR studies showed that conversion of homocysteine (the reduced, thiol form, RSH) to homocystine (the oxidized, disulfide form of homocysteine, RSSR) was enhanced in the presence of Compound 4. Additionally, the MALDI mass spectrum of products formed in a solution containing Compound 4 and Hcy exhibited prominent peaks for the sodium salt of glycine, and for the disodium and dipotassium salts of a glycine-derived dimer. Glycine and its dimerization products are known to be termination products of α-amino acid carbon-centered radicals. MALDI TOF MS (anthracene matrix), calculated for glycine sodium salt $C_2H_4NNaO_2$ $(M+Na)^+$ 97.01. found 96.89; calculated for glycine dimer (2,3-diaminosuccinic acid disodium salt) $C_4H_6Na_2N_2O_4$ $(M+2Na)^+$ 192.01. found 193.05; calculated for glycine dimer (2,3-diaminosuccinic acid dipotassium salt) $C_4H_6K_2N_2O_4$ $(M+2K)^+$ 223.96. found 223.86.

Example 4

The analysis of thiols in biological fluids has typically required a disulfide reduction step, often accomplished with a reducing agent such as a phosphine derivative. Disulfide radicals, as well as α-amino acid carbon-centered radicals may reduce species such as $MV^{2+}$. We have found that a reducing agent, such as $PPh_3$ or another phosphine, enhances the present process by inhibiting biothiol interference, leading to greater colorimetric selectivity. Additionally, $PPh_3$ and its congeners may undergo redox chemistry or reactions with thiols in the presence of electron acceptors (e.g., $MV^{2+}$).

When $PPh_3$ (5 equiv to thiol) was present in a 70% MeOH/$H_2O$ (phosphate buffer, pH=7.3) solution of Compound 4 ($10^{-5}$ M), the observed absorbance changed substantially only for Hcy. Substantial changes were not seen for Cys, nor for the related thiols glutathione or penicillamine. When a 30-fold molar excess of Cys (to Hcy) was added to a solution of Hcy (approximately the naturally-occurring proportion of Cys to Hcy in plasma) and Compound 4, no absorbance change was seen as compared to an otherwise identical solution lacking the Cys.

Without wishing to be bound by this theory, the reducing agent (e.g., $PPh_3$) apparently functioned to inhibit disulfide formation (i.e., thiol oxidation), which, in turn, inhibited thiol-promoted dye reduction. Beyond a threshold level of about 100 equiv $PPh_3$, Hcy-promoted absorbance changes were diminished. Only 45 equiv $PPh_3$ were needed to suppress the interaction of other thiols.

Figure 3:
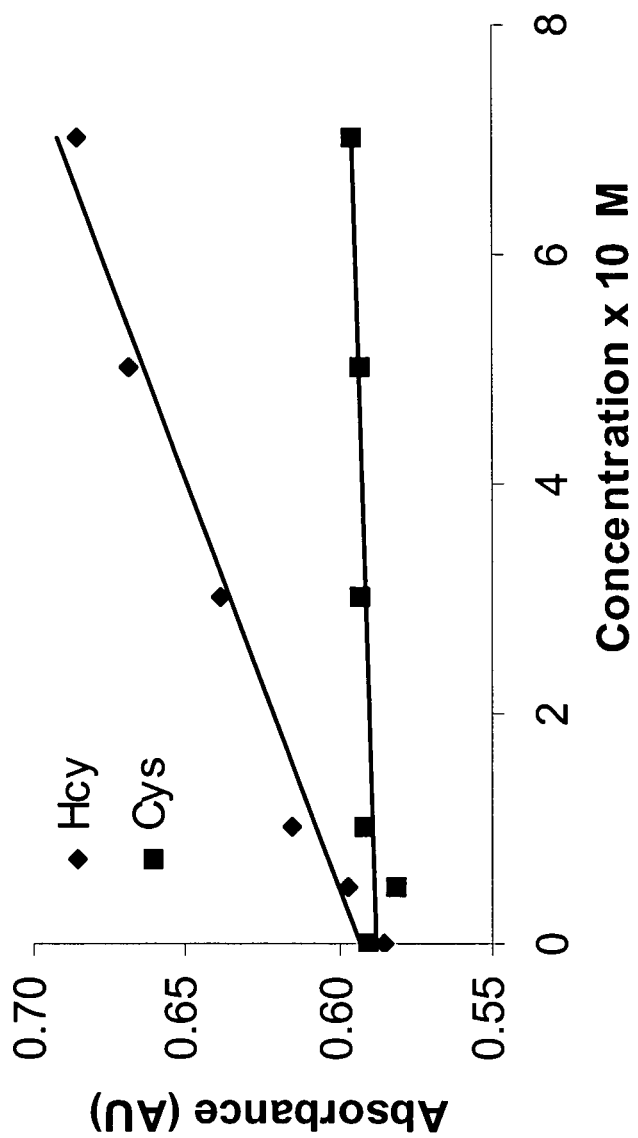
FIG. 3 depicts absorbance at 510 nm as a function of various concentrations of L-Cys and Hcy in solutions of Compound 4 and $PPh_3$.

FIG. 3 depicts absorbance at 510 nm as a function of various concentrations of L-Cys and Hcy in solutions of Compound 4 ($1.0\times10^{-5}$ M) and $PPh_3$ ($4.5\times10^{-4}$ M).

Thus, potential interferences from biothiols with Compound 4 or $MV^{2+}$ may be controlled by the addition of $PPh_3$ to afford selective detection for Hcy. (Note that interferences were not observed with $MV^{2+}$. The addition of a phosphine derivative, which helped reduce interferences with fluorone black, was not found to be necessary with $MV^{2+}$.)

If left standing for 24 h, solutions containing $PPh_3$, Hcy, and Compound 4 exhibited about a 50% reduction in absorption as compared to the spectrum of a fresh solution.

It should be noted that $PPh_3$ was chosen primarily because it was an inexpensive reducing agent that was readily available commercially. It may, if desired, be replaced with another phosphine, as phosphines generally will react with thiols in a similar manner. Phosphines liberate thiols such as cysteine and homocysteine from proteins via a disulfide reduction, thus facilitating analysis of thiol content in a sample. Phosphines thus play a convenient dual role in this method, both affording enhanced selectivity and liberating bound thiols from proteins. More generally, other disulfide reducing agents may be used, e.g., sodium borohydride or sodium triacetoxyborohydride.

Example 5

Compound 4 may be used, for example, as a colorimetric agent in the determination of total Hcy in human plasma. Commercial lyophilized human blood plasma was reconstituted with distilled $H_2O$ (5.0 mL). Bound thiols were liberated from proteins by stirring the plasma solution in a commercially-available disulfide reducing gel, TCEP (tris[2-carboxyethyl]phosphine hydroxide). This was followed by deproteinization upon addition of MeOH containing $PPh_3$ ($1.5\times10^{-3}$ M). After centrifugation (5 min, 3000 g) the supernatant was filtered through a cellulose filter having a 3000 MW cutoff. Different Hcy standards in $H_2O$ (0.3 mL, pH=7.3, phosphate buffer) containing Compound 4 were added to the filtrate. To determine recovery percentages, known amounts of Hcy were added to plasma samples before the reduction and deproteinization steps, and the resulting differences in absorbance as compared to the original sample were correlated with Hcy concentrations from the calibration curve. The concentration of Hcy in the commercial plasma sample was determined from the calibration curve by subtracting the absorbance of a solution containing Compound 4 and $PPh_3$ from the absorbance of the plasma sample mixed with Compound 4 and $PPh_3$. The total Hcy content in the original commercial plasma sample was found to be 3 µM.

Figure 4:
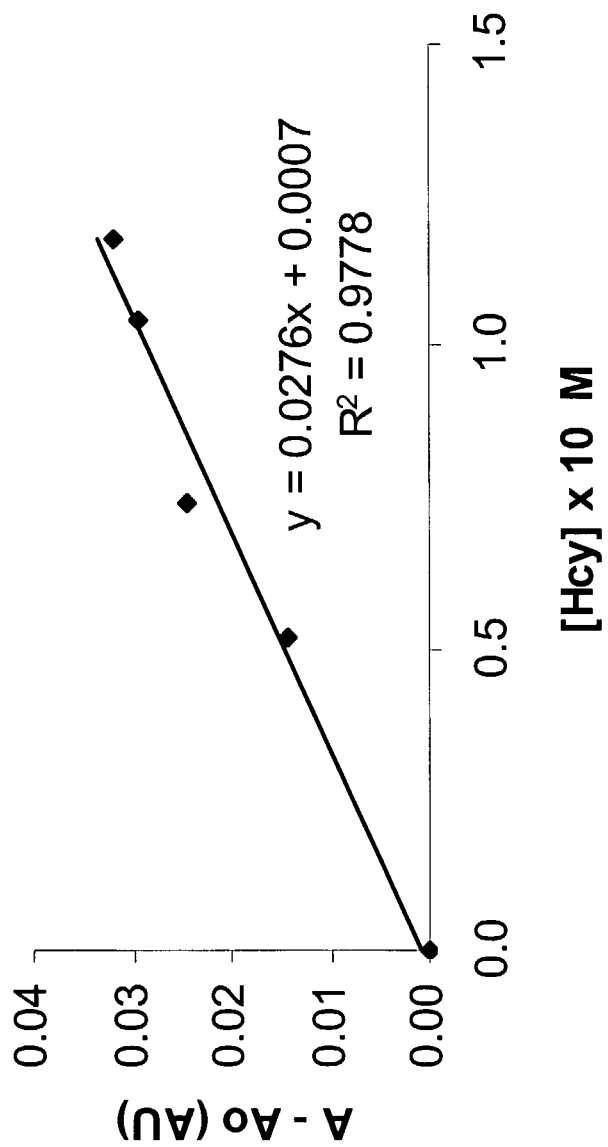
FIG. 4 depicts a calibration curve derived from solutions containing added Hcy standards: absorbance at 510 nm versus Hcy concentrations in human plasma in the presence of $PPh_3$ and Compound 4, after reduction and deproteinization, using an indirect standard addition approach.

FIG. 4 depicts a calibration curve derived from solutions containing added Hcy standards: absorbance at 510 nm versus Hcy concentrations in human plasma in the presence of $PPh_3$ and Compound 4 after reduction and deproteinization, using an indirect standard addition approach. A denotes the absorbance of the plasma sample with added Hcy, and Ao is the absorbance of a plasma sample without added standards. The curve showed linearity in a working range from 0 to 15 µM, which includes the range for normal Hcy concentrations in humans (up to about 12 µM; by contrast, typical Cys concentrations are about 20-30 times higher). The percentage recovery of Hcy was 102.9%±7.3%. The relative standard deviation (RSD) was 7.1% (n=3). Straightforward extension of these measurements will be used to calibrate absorbance versus Hcy concentration in plasma for concentrations beyond the range shown in FIG. 4.

Example 6

In addition to $MV^{2+}$ and fluorone black, the present method for specifically determining homocysteine will work with a wide variety of other electron-accepting, aromatic chromophores and fluorophores, specifically, those whose redox potentials allow the chromophore or fluorophore to readily accept an electron from homocysteine. The aromatic resonance helps to stabilize the radical that results when the chromophore or fluorophore accepts an electron. Examples of such electron-accepting, aromatic chromophores and fluorophores include rhodamines, or other xanthenes and substituted xanthenes such as the following:

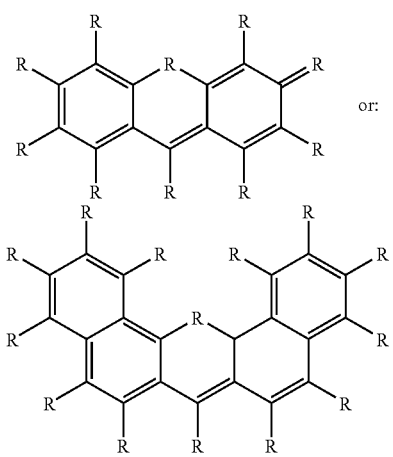

wherein the R groups may be the same or different; and each of the Rs may, for example, be independently selected from the group consisting of halogen, metal, alkyl, vinyl, alkynyl, aromatic, H, N, S, C, O, B, P, or Si, singly or multiply bonded, oligomer or polymer; and it is understood that normal valences and oxidation states are preserved. Where appropriate to satisfy normal valences and oxidation states, it should be understood that one or more hydrogen atoms may be bonded to the listed substituents as appropriate (e.g., OH, $CH_2$, $CH_3$, etc.)

Other examples of such electron-accepting, aromatic or conjugated orotherchromophores and fluorophores, such as one or more of the following ammonium cations:

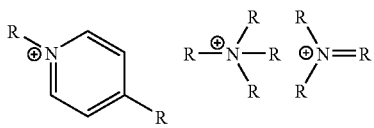

wherein the R groups may be the same or different; and each of the Rs may, for example, be independently selected from the group consisting of halogen, metal, alkyl, vinyl, alkynyl, aromatic, H, N, S, C, O, B, P, or Si, singly or multiply bonded, oligomer or polymer; and it is understood that normal valences and oxidation states are preserved. Where appropriate to satisfy normal valences and oxidation states, it should be understood that one or more hydrogen atoms may be bonded to the listed substituents as appropriate (e.g., OH, $CH_2$, $CH_3$, etc.)

In lieu of measuring absorbance or fluorescence spectra, as was done in the above examples, one may also determine homocysteine using the method and compounds as otherwise described above, but instead by measuring the change in redox potential as a function of homocysteine concentration.

Determination of Homocysteine and Cysteine

Figure 5:
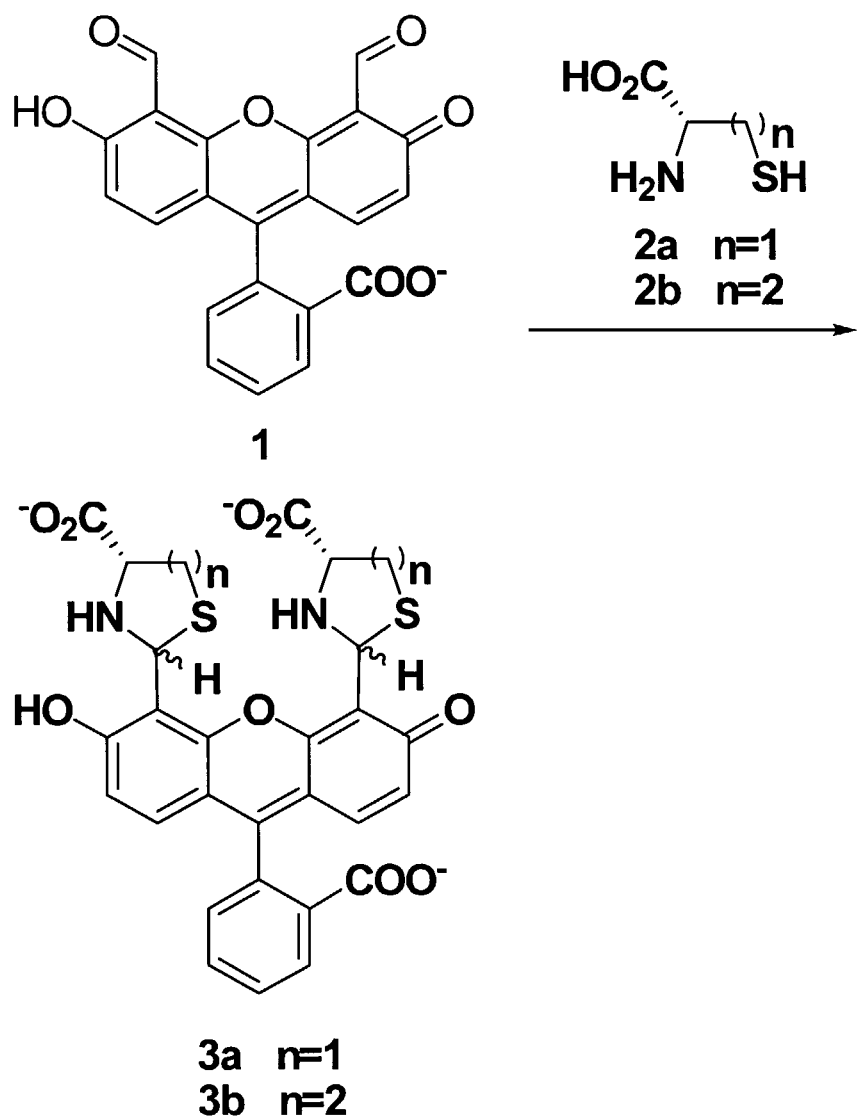
FIG. 5 depicts the reaction of xanthene 1 with cysteine (2a) or homocysteine (2b) to form the spectroscopically distinct species 3a or 3b.

We have also discovered that xanthene dye 1 (or other indicator species, as discussed further below) may be used for the efficient determination of cysteine and homocysteine. FIG. 5 depicts the reaction of xanthene 1 with cysteine or homocysteine to form the spectroscopically distinct species 3a or 3b. The formation of these species may be monitored colorimetrically or fluorometrically. They may be selectively detected by visible, near-infrared, or ultraviolet absorbance or fluorescence spectroscopy. As compared to the above method for determining homocysteine alone, this method allows the use of a broader range of pH and solvents, including, for example, polar protic solvents and polar aprotic solvents or mixtures of such solvents, including water, DMF, DMSO, acetone, THF, EtOH, MeOH, acetonitrile, and the like, and a pH between about 5 and about 13.

The synthesis of Compound 1 is described in S. Burdette et al., "Fluorescent sensors for $Zn^{2+}$ based on a fluorescein platform: Synthesis, properties and intracellular distribution," *J. Am. Chem. Soc.*, vol. 123, pp. 7831-7841 (2001). This published method requires a seven-step synthesis. Other work in our laboratory has recently discovered a single-step synthesis of Compound 1, as well as its monoaldehyde analog. Briefly, commercially-purchased fluorescein was dissolved in a 50% aqueous NaOH solution, to which MeOH was then added. After the fluorescein had dissolved, tributylamine and $CHCl_3$ were added, and stirred at 55° C. for five hours. Then the reaction mixture was cooled to room temperature. The solution was acidified with 10 M $H_2SO_4$ to pH 1. The precipitate was filtered out, dried under vacuum, and then purified by flash chromatography to separate mono- and dialdehyde using a 15/85 EtOAc/DCM mixture. X-ray crystallography confirmed the structures of both the mono- and dialdehydes.

Example 7

Following the addition of cysteine or homocysteine (1.0× $10^{-3}$ M) to a solution of Compound 1 (1.0×$10^{-6}$ M, $H_2O$, pH 9.5), the solution changed color from bright yellow to brownish-orange. Similar color changes were observed on $C_{1-8}$-bonded silica. UV-Vis absorbance changes of cysteine-Compound 1 solutions, readily monitored in the $10^{-5}$ to $10^{-6}$ M cysteine concentration range, exhibited a 25 nm red shift. Adding cysteine or homocysteine to Compound 1 also resulted in fluorescence quenching. By contrast, little or no color change was observed upon addition of bovine serum albumin, glycine, or N-propylamine to a solution of Compound 1. We also observed analogous absorption spectra under identical conditions at pH 6.5; however, at the lower pH we also observed minor amounts of precipitate.

Example 8

The conversion of cysteine (Compound 2a) and of homocysteine (Compound 2b) to thiazolidine dicarboxylic acids 3a and 3b, respectively, was confirmed by $^1H$ NMR. The reaction of Compound 1 with propylamine or glucosamine (in a 1:2 ratio of Compound 1 to the analyte, in $D_2O$) resulted in a diminishing aldehyde resonance (10.2 ppm) for Compound 1, and in the appearance of imine resonances centered at 9.6 ppm. When Compound 2a or 2b was added to solutions of Compound 1, imine resonances were observed at ca. 9.6 ppm, resonances that diminished overtime (5 min). New resonances centered at 6.13 ppm and 6.04 ppm appeared, which were assigned to the methine protons of the thiazolidine diastereomers 3a and 3b, respectively. Complete conversion to the bis-thiazolidines 3a and 3b was evidenced by a 2:2:1 ratio of the integrated areas of the new methine protons to the chromophore aromatic proton resonances, as well as by the complete disappearance of the starting aldehyde and intermediate imine resonances. No evidence was observed for the formation of any aromatic heterocycle. The formation of species 3a and 3b was also confirmed by mass spectrometry: Compound 3a MALDI TOF MS, calculated for $C_{28}H_{21}N_2O_9S_2Na$ (M+Na)+ 618.61. found 618.42; Compound 3b FAB MS, calculated for $C_{30}H_{25}N_2O_9S_2Na$ (M+Na)+ 646.66. found 646.80.

Example 9

Figure 6:
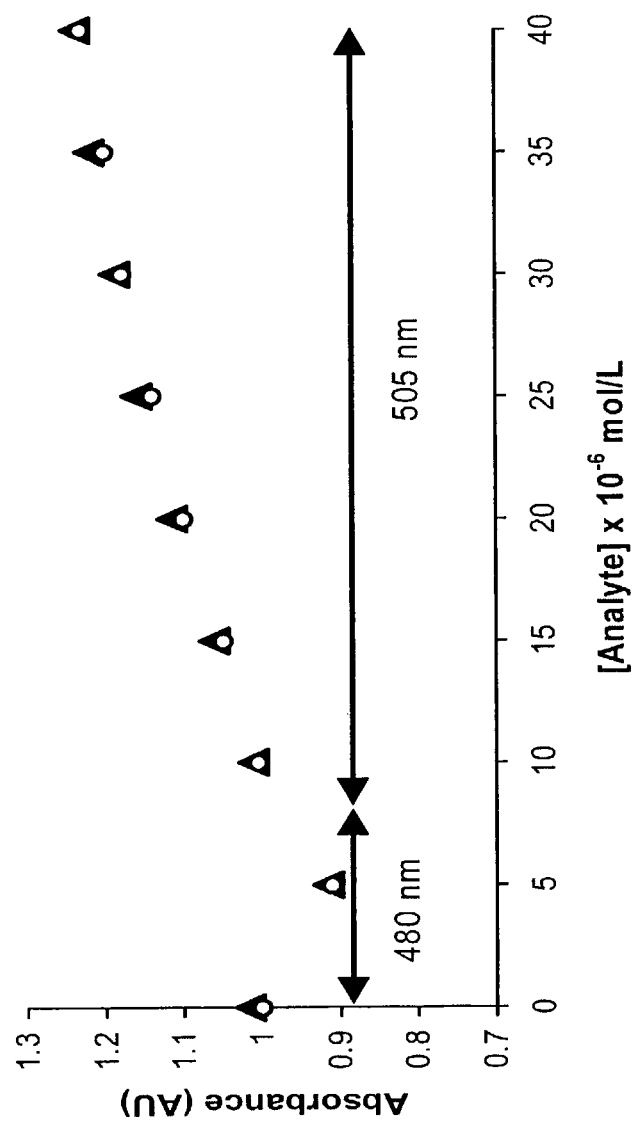
FIG. 6 depicts plots of absorbance versus concentration for L-cysteine (solid triangles) and homocysteine (open circles) in aqueous solutions of Compound 1 at pH 9.5.

FIG. 6 depicts plots of absorbance versus concentration for cysteine (solid triangles) and homocysteine (open circles) in aqueous solutions of Compound 1 ($2.5 \times 10^{-6}$ M) at pH 9.5. Note the high degree of similarity in the absorbance responses of Compound 1 to cysteine and to homocysteine. Thus this particular assay will detect and quantitate total cysteine and homocysteine in a sample, but it does not distinguish between cysteine and homocysteine. Note that for a lower range of concentrations, 0 through $5.0 \times 10^{-6}$ M, FIG. 6 depicts the decrease in absorbance at 480 nm, while at the higher concentrations of $10.0 \times 10^{-6}$ M and above, FIG. 6 depicts the increase in absorbance at 505 nm. The change in the wavelength being monitored reflects the red shift in the spectrum of Compound 1 caused by increasing concentrations of Cys or Hcy. Due to this red shift, more accurate measurements of Cys or Hcy concentration may be made at lower concentrations (below about $10 \times 10^{-6}$ M) by observing the decrease in absorbance at 480 nm, and more accurate measurements of concentration may be made at higher concentrations (above about $1.0 \times 10^{-5}$ M) by observing the increase in absorbance at 505 nm.

Example 10

Figure 7:
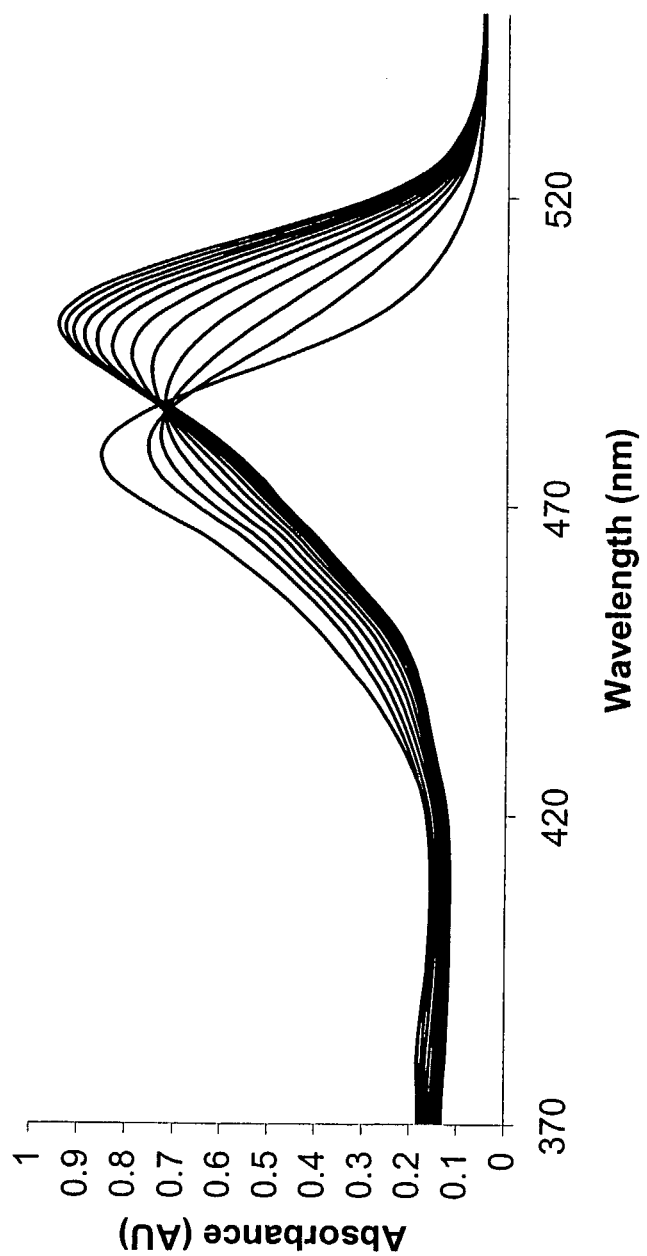
FIG. 7 depicts the red shift in absorbance in the UV-Vis absorption spectrum at room temperature of Compound 1 at various concentrations of cysteine in deproteinized human plasma containing an excess of added glutathione (pH 9.5).

The red shift in absorbance is depicted in FIG. 7, which shows the UV-Vis absorption spectrum at room temperature of Compound 1 ($4 \times 10^{-6}$ M) at concentrations of L-cysteine ranging from $4.9 \times 10^{-5}$ to $7.4 \times 10^{-4}$ M in deproteinized human plasma (previously centrifuged at 3000 g through a cellulose 3000 MW cut-off filter, with the low molecular weight fraction used for analysis), containing an excess (1.0 mM) of added glutathione (pH 9.5). Each spectrum was taken 5 min after cysteine addition. As the concentration of L-cysteine increased, a red shift was observed in the absorption spectrum from about 480 nm to about 500 nm.

UV-Vis spectra of solutions containing Compound I and other common thiols (L-methionine, mercaptoethanol, glutathione), other amino acids (L-glutamine, L-serine, glycine, L-glutamic acid), and other amines (D-glucosamine hydrochloride and N-propylamine) ($8.0 \times 10^4$ M in all cases, pH 9.5) showed no substantial changes in the absorption spectrum of Compound 1 between 370 and 520 nm (data not shown). These data confirmed the selectivity of Compound 1 for cysteine and homocysteine. More specifically, there was at most a 15% change in absorbance at 480 nm in response to any of these other analytes, and no shift in the wavelength of the absorption peak. Likewise, solutions containing Compound 1 and bovine serum albumin or urease ($8.0 \times 10^{-4}$ M, pH 9.5) also showed relatively small absorbance changes (less than 15%), and no shift in wavelength (data not shown). Potential interferences were not observed.

Example 11

Figure 8:
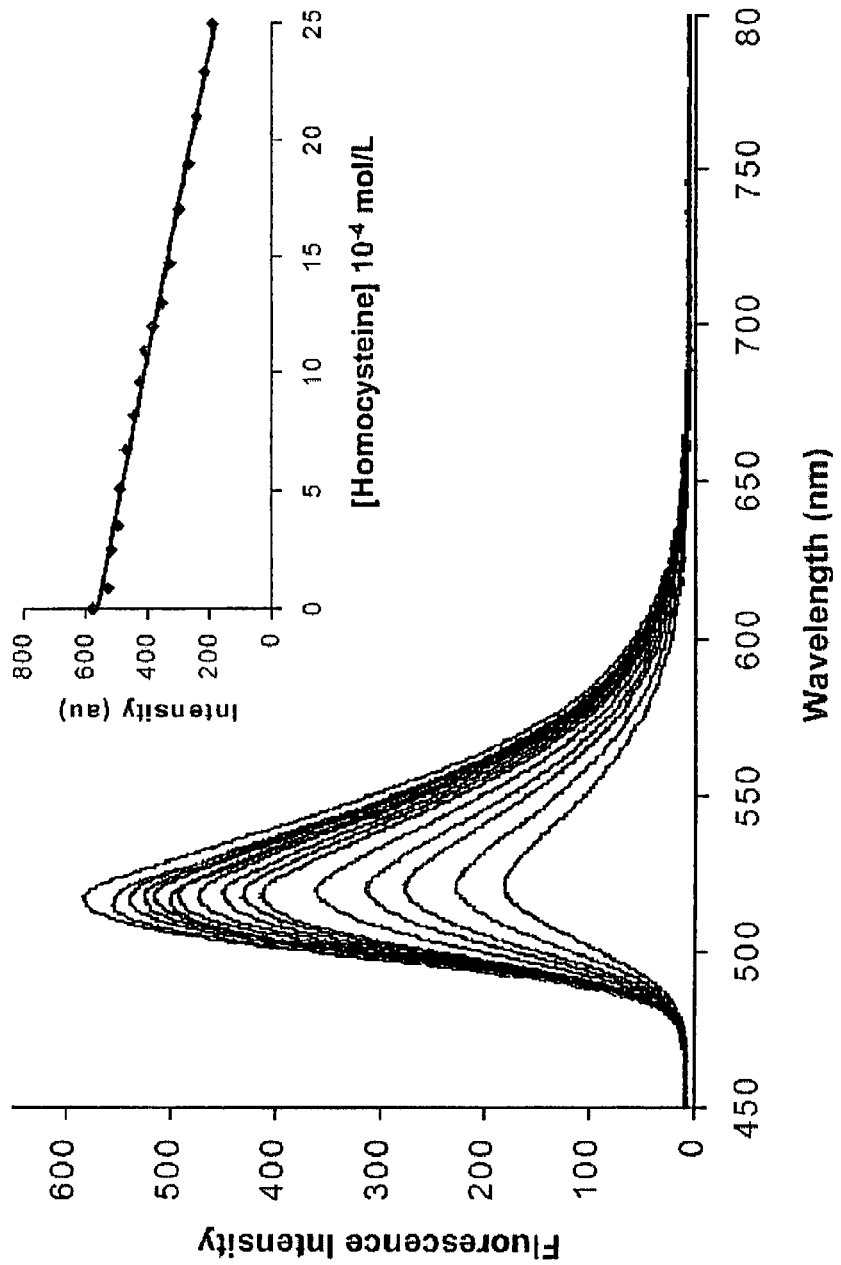
FIG. 8 depicts fluorescence emission spectra of Compound 1 and homocysteine in deproteinized human plasma (pH 9.5), with excitation at 460 nm. The inset depicts the intensity of fluorescence emission versus homocysteine concentration.

FIG. 8 depicts fluorescence emission spectra of Compound 1 ($5.2 \times 10^{-7}$ M) and homocysteine ($2.9 \times 10^{-6}$ to $2.5 \times 10^{-3}$ M) in deproteinized human plasma (pH 9.5), with excitation at 460 nm. The inset depicts the intensity of fluorescence emission versus homocysteine concentration. As shown in the inset, there was a nearly linear correlation between fluorescence emission intensity and homocysteine concentrations over the physiologically significant range shown. These data demonstrate the utility of Compound 1 in determining and calibrating concentrations of cysteine and homocysteine in plasma samples, even in the presence of other biological thiols. Interference from amines, amino acids and certain thiols and proteins was found to be minimal. Similar spectral changes were observed in plasma that had been deproteinized using MeOH or MeCN, thereby bypassing the need for a centrifugation step.

Example 12

In addition to Compound 1, it is believed that the present method for specifically determining homocysteine and cysteine will work with a wide variety of conjugated chromophores and fluorophores having at least one aldehyde functionality, where the aldehyde functionality is conjugated with at least one carbon-carbon double bond. Examples of such conjugated chromophores and fluorophores having at least one aldehyde functionality include the following:

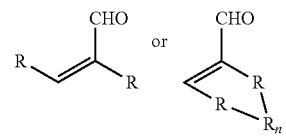

wherein the R groups may be the same or different; and each of the Rs may, for example, be independently selected from the group consisting of halogen, metal, alkyl, vinyl, alkynyl, aromatic, H, N, S, C, O, B, P, or Si, singly or multiply bonded, oligomer or polymer; and it is understood that normal valences and oxidation states are preserved. Where appropriate to satisfy normal valences and oxidation states, it should be understood that one or more hydrogen atoms may be bonded to the listed substituents as appropriate (e.g., OH, $CH_2$, $CH_3$, etc.) The "n" represents an integer between 1 and 8, and the various R groups designated by "$R_n$" may be the same or different.

Determination of Cysteine

We have also discovered that 4-(dimethylamino)cinnamaldehyde (or other indicator species, as discussed further below) may be used for the efficient determination of cysteine. Cysteine may be determined colorimetrically or fluorometrically, by visible, near-infrared, or ultraviolet absorbance or fluorescence spectroscopy. This method is selective for cysteine, even in a homocysteine background.

Figure 9:
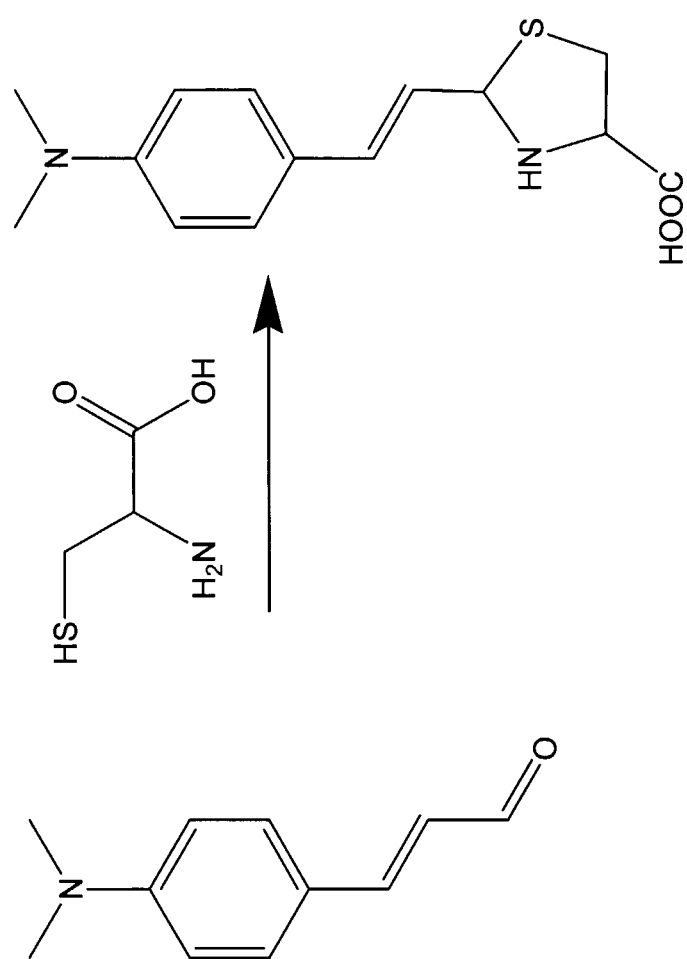
FIG. 9 depicts the proposed reaction of cysteine with 4-(dimethylamino) cinnamaldehyde.

FIG. 9 depicts a proposed mechanism for the reaction of cysteine with N-dimethylamino cinnamaldehyde.

Example 13

The interactions of 4-(dimethylamino)cinnamaldehyde with cysteine and homocysteine were monitored by UV/V is spectroscopy. UV/V is absorption spectra were recorded in 0.1 M aqueous sodium carbonate buffer (pH 9.5). The concentration of the dye (4-(dimethylamino)cinnamaldehyde) was $5.7 \times 10^{-6}$ M. The concentration of amino acid (L-cysteine in this example, or homocysteine in Example 14 below) varied from $4.5 \times 10^{-5}$ to $3.4 \times 10^{-3}$ M. A color change was seen visually. The solution was yellow in the absence of cysteine, and became increasingly paler in color as the cysteine concentration increased, becoming essentially colorless at the highest cysteine concentration tested. FIG. 10(a) shows the decrease in a broad absorbance peak at 395 nm with increasing concentrations of L-cysteine, measured 10 minutes after addition of the cysteine.

Example 14

Figure 10B:
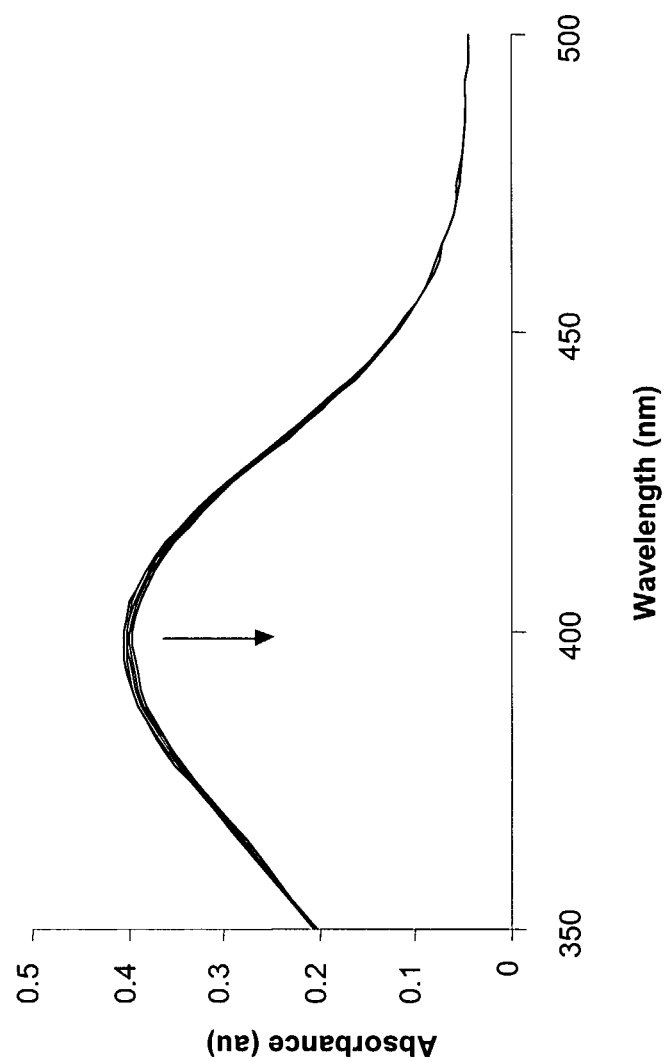

The procedures of Example 13 were repeated, using homocysteine instead of L-cysteine. At homocysteine concentrations from $4.5 \times 10^{-5}$ to $3.4 \times 10^{-3}$ M, no color change was seen visually. The UV/V is absorption spectrum shown in FIG. 10(b) likewise shows essentially no change in the 395 nm absorbance peak. (NMR data, not shown, demonstrated that the reaction of the racemic DL-homocysteine mixture with the dialdehyde proceeded to completion, thus ruling out the unlikely possibility that the observed differences between Examples 13 and 14 might have resulted from the use of an enantiomerically-pure analyte in Example 13, and a racemic mixture in Example 14.)

Example 15

The procedures of Example 13 were repeated with other control analytes in lieu of cysteine, namely, L-methionine, L-serine, glycine, L-glutamic acid, L-glutamine, mercaptoethanol, D-glucosamine and bovine serum albumin. No color change was observed for any of these analytes visually, nor were any significant changes seen in the 395 nm absorbance peaks of the aldehyde.

Example 16

The specificity of 4-(dimethylamino)cinnamaldehyde for cysteine is useful in the determination of cysteine in a background that may have closely related compounds, such as biological samples also containing homocysteine and other amino acids. Where dyes specific for different compounds have distinct spectral ranges, they may be used simultaneously for determining different compounds simultaneously. For example, the ~400 nm absorbance peak of 4-(dimethylamino)cinnamaldehyde does not overlap substantially with the ~500 nm peak for fluorescein dialdehyde. Thus, 4-(dimethylamino)cinnamaldehyde has been used in conjunction with fluorescein dialdehyde to detect cysteine alone at ~400 nm, and total cysteine plus homocysteine at ~500 nm. The concentration of homocysteine may then be inferred as [Hcy]=[Hcy+Cys]−[Cys]. (data not shown).

Examples 17-21

Optionally, the novel detection methods may be coupled in-line as part of a detector in an analytical system, for example as a post-column HPLC detection system, in which analytes are determined in one or more reactors containing one or more selective indicators in accordance with the present invention. These methods may also be used in a sensor array system, i.e., using a group of dyes that give different signals for the same or different analytes.

For example, we have successfully conducted several HPLC post-column detection experiments. The general reaction conditions and equipment were as follows: An RDR-1 reagent delivery/reaction module (Timberline) was equipped with a 110B solvent delivery module (Beckman) and a SpectroMonitor 3200 UV-Vis detector (LDC/Milton Roy), using a LiChrospher 100 RP-18 end-capped column (4.6 mm×250 mm, Alltech Associates Inc.), particle diameter: 5 µm. The RDR-1 unit comprised a reagent reservoir pressurized by helium gas, a mixing tee, and a Teflon reaction coil (0.02" ID×1 m, or 0.02" ID×2 m, with nominal volume 0.2 ml or 0.4 ml, respectively), all cast in a tin alloy reaction block with thermostat. The mobile phase was 100% HPLC-grade water. The reagents were injected at a flow rate of 1.5 mL/min. Other conditions specific to the different experiments are described below.

When we used fluorone black as a post-column detection reagent, the reactor temperature was 80° C.; fluorone black was dissolved to a final concentration of $1.25 \times 10^{-5}$ M in a 50%/50% (v/v) mixture of methanol and pH 9.5 aqueous carbonate buffer, and absorbance was monitored at a wavelength of 505 nm. FIG. 11(a) depicts the two sharp peaks that were observed when 28.8 nmol each of cysteine and homocysteine were injected. By contrast, FIG. 11(b) depicts the absorbance seen with equimolar amounts of the three amino acids histidine, methionine, and glutamine; and FIG. 11(c) depicts the absorbance seen with equimolar amounts of the three amino acids lysine, glycine, and serine. As seen in these plots, there was strong and specific detection of cysteine and homocysteine, without significant interference from other amino acids.

When we used fluorescein dialdehyde as a post-column detection reagent, the reactor temperature was 80° C.; fluorescein dialdehyde was dissolved to a final concentration of $6.4 \times 10^{-5}$ M in 0.125 M of pH 9.5 aqueous carbonate buffer, and absorbance was monitored at a wavelength of 510 nm. FIG. 11(d) depicts the two sharp peaks that were observed when 87 nmol each of cysteine and homocysteine were injected.

When we used methyl viologen as a post-column detection reagent, the reactor temperature was 80° C.; 0.01 M methyl viologen was dissolved to a final concentration of 0.01 M in 0.25 M of pH 9.5 aqueous carbonate buffer; and the mobile phase included 0.01 M TFA. Absorbance was monitored at a wavelength of 610 nm. FIG. 11(e) depicts the two sharp peaks that were observed when 173 nmol each of cysteine and homocysteine were injected.

Example 22

A preferred method for the determination of homocysteine in human blood plasma is described below. This streamlined method uses methyl viologen as the reagent, and does not require deproteinization of the plasma.

First, disulfide bonds in the plasma were reduced. Immobilized TCEP disulfide reducing gel (catalog number: 77712, Pierce, Rockford, Ill.) was used as the reducing agent. The TCEP gel was packed into a disposable 10 mL polypropylene column (catalog number: 29924, Pierce, Rockford, Ill.) following the manufacturer's recommended protocols. The plasma was reconstituted with distilled water. The plasma was applied to the packed column, and the column was incubated at room temperature as recommended by the manufacturer. The reduced plasma was then eluted through the column with tris buffer (pH 3.9-8.3).

An aliquot of reduced plasma was then mixed with a solution of methyl viologen in tris buffer. The mixture was gently heated on a hot plate or in a microwave to promote color formation. The concentration of Hcy was determined by measuring the intensity of the blue color formed (e.g., absorbance at 610 nm, or by visual inspection).

Example 23

We have also discovered a preferred method for the highly selective detection of homocysteine using a combination of aldehydes. For example, we have used the xanthene dye Compound 1, and N-dimethylamino cinnamaldehyde (Compound 6) in the efficient detection of homocysteine. Compound 6 was used as a scavenger for cysteine, making the determination of homocysteine with Compound 1 more efficient.

A color change was readily observed visually when L-cysteine ($1.0 \times 10^{-3}$ M) was added to a solution of Compound 6 ($1.0 \times 10^{-6}$ M, $H_2O$, pH 9.5). To the unaided eye, the initially yellow solution became colorless after 10 minutes for L-cysteine, but remained unchanged (yellow) both for L-homocysteine and for a negative control to which no analyte was added. We also observed that related compounds such as cinnamaldehyde and p-nitrocinnamaldehyde demonstrated a tendency at the same conditions to react preferentially with cysteine or homocysteine over other thiols. N,N-dimethylcinnamaldehyde reacted preferentially with cysteine over homocysteine or other thiols.

We also monitored the interaction of cysteine and homocysteine with Compound 6 by UV-Vis and fluorescent spectroscopy. Compound 6 reacted quickly with cysteine to form the colorless products Compounds 7 and 8. See FIG. 12. Under the conditions employed, we observed no significant fluorescence from Compound 6, nor from its derivatives Compounds 7 and 8. Because Compound 6 had differing selectivity for cysteine and homocysteine, and because Compounds 6, 7, and 8 all lack significant fluorescence, we found that a combination of aldehydes 6 and 1 was particularly effective for detecting homocysteine, because Compound 6 acted as a scavenger of cysteine, allowing Compound 1 react primarily with homocysteine.

We observed that the level of fluorescence emission from Compound 1 was significantly quenched by the presence of cysteine, but not by the presence of Compound 6 alone. Further, when Compound 6 was pre-incubated with cysteine before the addition of Compound 1, the fluorescence emission of Compound 1 was virtually unchanged. (data not shown) Thus Compound 6 acted as an effective scavenger, to remove potential interference from cysteine in determining homocysteine.

We have demonstrated the practical use of this method with experiments using deproteinized plasma solutions in carbonate buffer, pH 9.5. An analytical signal was observed for homocysteine only when three different samples were tested: one containing cysteine, one containing homocysteine, and one containing a mixture of both cysteine and homocysteine. Each sample was pre-incubated for 20 minutes at room temperature with Compound 6 (molar ratio, analyte:Compound 6=1:2). Following the pre-incubation Compound 1 was added. Our results indicated that all added cysteine was consumed by reaction with a molar excess of Compound 6. By contrast, when the plasma sample was not pre-incubated with Compound 6, cysteine in the plasma as well as homocysteine reacted with Compound 1, as shown in FIG. 5, leading to interfering fluorescence quenching. The observed fluorescence quenching was dependent on the concentration of homocysteine in the sample, and was not strongly affected by the presence of Compound 6.

See FIG. 13, depicting the results of this experiment with Compounds 6 and 1. FIG. 13 depicts fluorescence emission spectra of fluorescein dialdehyde ($1.7 \times 10^{-7}$ M) and N-dimethylamino cinnamaldehyde ($2 \times 10^{-4}$ M) in deproteinized blood plasma, with different analytes. The top curve is for $1.3 \times 10^{-4}$ M cysteine. The second curve, barely distinguishable from the top curve, is a control with no analytes. The third curve is for a mixture of $1.3 \times 10^{-4}$ M cysteine and $1.3 \times 10^{-4}$ M homocysteine. The bottom curve is for a mixture of $1.3 \times 10^{-4}$ M cysteine and $6.5 \times 10^{-4}$ M homocysteine. Note that as the concentration of homocysteine increased, fluorescence quenching increased. No significant interference was seen from cysteine.

This technique allows one to specifically estimate the level of homocysteine in blood samples or other samples. A deproteinization step should not be needed, and should be optional, because Compound 6 in molar excess should react with cysteine and with any other groups that might potentially react with an aldehyde and cause interference, but Compound 6 does not react with homocysteine.

More generally, the cysteine-scavenger may be selected from the group consisting of one or more of the following:

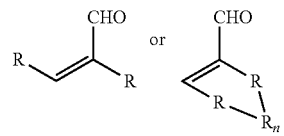

wherein the R groups may be the same or different; and each of the Rs is independently selected from the group consisting of halogen, metal, alkyl, vinyl, alkynyl, aromatic, H, N, S, C, O, B, P, and Si; wherein the R groups may be singly or multiply bonded; wherein the R groups may comprise monomer, oligomer or polymer; where normal valences and oxidation states are satisfied; and wherein one or more hydrogen atoms may be bonded to one or more of the R groups to satisfy normal valences and oxidation states; and wherein n denotes an integer from 1 to 8; and wherein at least one of the R groups is an electron donor.

Example 24

The stability of a solution of Compound 1 in 0.1 M carbonate buffer ($10^{-6}$ M) was measured. After storage for 2 weeks at room temperature, followed by reaction with cysteine or homocysteine, only 9% of the original change in the absorbance signal was lost. Thus the solutions are relatively stable over time, although they may lose activity over a period of months.

Example 25

Compound I may also be used in the calorimetric detection of N-cys terminal peptides. UV-Vis studies of the dipeptide cys-gly with Compound 1 displayed approximately the same red shift as for L-cys alone. Thus Compound I may be used as a specific reagent for labeling N-terminal cysteine-containing peptides or proteins.

Miscellaneous.

The complete disclosures of all references cited in the specification are hereby incorporated by reference. Also incorporated by reference are the complete disclosures of each of the following references, none of which is prior art to this application: O. Rusin et al., "Visual Detection of Cysteine and Homocysteine," *J. Am. Chem. Soc.*, vol. 126, pp. 438-439, including its associated Supporting Information (2004, published on Web Dec. 19, 2003); W. Wang et al., "Direct Detection of Homocysteine," *J. Am. Chem. Soc.*, vol. 126, pp. 3400-3401, including its associated Supporting Information (published on Web Mar. 2, 2004); and N. St. Luce, "Optical Detection of L-Cysteine and L-Homocysteine via a Fluorescein Derivative," Chapter 5, pages 59-79, in *Synthesis, Characterization and Study of Novel Reagents for the Detection of Saccharides and Amino Acids*, PhD Dissertation, Louisiana State University (Baton Rouge, La., 2004). In the event of an otherwise irreconcilable conflict, however, the present specification shall control.

What is claimed:

1. A process for selectively determining the concentration of homocysteine in a substance, said process comprising the steps of:

(a) preparing an aqueous solution comprising a sample of the substance and a dye at a temperature between about 25° C. and about 110° C., and a pH between about 6 and about 8;
(b) observing any perturbation in the visible, near infrared, or ultraviolet absorbance spectrum or fluorescence spectrum of the dye; or observing any perturbation in the redox potential of the solution; in either case as compared to the spectrum or redox potential of an otherwise identical and otherwise identically treated solution of the dye that lacks any added homocysteine; and
(c) inferring the homocysteine concentration from a previously-determined correlation between observed perturbations in the spectrum or the redox potential of the dye, and the homocysteine concentration;
wherein the dye comprises fluorone black.

2. A process as recited in claim 1, wherein the pH is about 7.5.

3. A process as recited in claim 1, wherein the solution additionally comprises a reducing agent.

4. A process as recited in claim 3, wherein the reducing agent comprises a phosphine.

5. A process as recited in claim 1, wherein the substance comprises plasma.

6. A process for selectively determining the concentration of homocysteine in a substance, said process comprising the steps of:
(a) preparing an aqueous solution comprising a sample of the substance and methylviologen at a pH between about 6 and about 8;
(b) observing any perturbation in the absorbance spectrum of the methylviologen as compared to the spectrum of an otherwise identical and otherwise identically treated solution of methylviologen that lacks any added homocysteine;
(c) inferring the homocysteine concentration from a previously-determined correlation between observed perturbations in the spectrum of methylviologen and the homocysteine concentration; and
(d) reversibly altering the absorbance spectrum of the methylviologen, by heating the solution from a temperature below about 40° C. to a temperature above about 40° C., or by cooling the solution from a temperature above about 40° C. to a temperature below about 40° C.; or both; whereby above about 40° C. the absorbance spectrum at 398 nm and at 605 nm selectively responds to the concentration of any homocysteine in the solution, and below about 40° C. the absorbance spectrum at 398 nm and at 605 nm is largely independent of the concentration of any homocysteine in the solution.

7. A process as recited in claim 6, wherein the substance comprises plasma.

8. A process for selectively determining the combined concentration of homocysteine and cysteine in a substance, said process comprising the steps of:
(a) mixing a sample of the substance with a solution comprising a dye at a pH between about 4 and about 12, at a temperature between about 0° C. and about 100° C.;
(b) observing any perturbation in the near-infrared or visible absorbance spectrum or fluorescence spectrum of the dye as compared to the spectrum of an otherwise identical and otherwise identically treated solution of the dye that lacks any added homocysteine and that lacks any added cysteine; and
(c) inferring the total homocysteine and cysteine concentration from a previously-determined correlation between observed perturbations in the spectrum of the dye and total homocysteine and cysteine concentration;

wherein the dye comprises

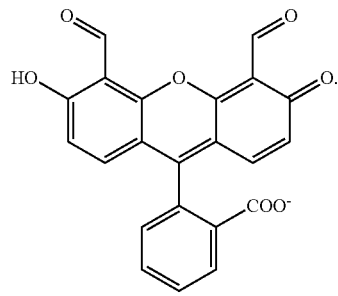

9. A process as recited in claim 8, wherein the substance comprises plasma.

10. A process for selectively determining the concentration of non-disulfide-linked, N-cysteine-terminal peptides in a substance, said process comprising the steps of:
(a) mixing a sample of the substance with a solution comprising a dye at a pH between about 4 and about 12, at a temperature between about 0° C. and about 100° C.;
(b) observing any perturbation in the near-infrared or visible absorbance spectrum or fluorescence spectrum of the dye as compared to the spectrum of an otherwise identical and otherwise identically treated solution of the dye that lacks any added N-cysteine-terminal peptides; and
(c) inferring the total N-cysteine-terminal peptide concentration from a previously-determined correlation between observed perturbations in the spectrum of the dye and total N-cysteine-terminal peptide concentration;
wherein:
the dye comprises

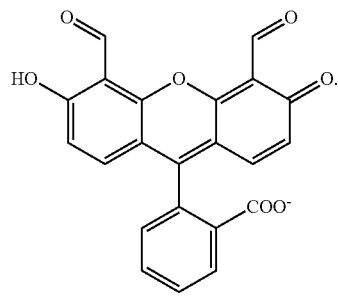

11. A process as recited in claim 10, wherein the pH is between about 6.5 and about 9.5.

12. A process as recited in claim 10, wherein the solution comprises a solvent selected from the group consisting of water, dimethylformamide, dimethylsulfoxide, acetone, tetrahydrofuran, methanol, ethanol, and acetonitrile.

13. A process as recited in claim 10, wherein said process is conducted in the presence of atmospheric oxygen.

14. A process for selectively determining the concentration of homocysteine in a substance in the presence of cysteine, said process comprising the steps of:
(a) mixing a sample of the substance with a cysteine-scavenger, wherein the cysteine-scavenger comprises 4-(N,N-dimethylamino)cinnamaldehyde;
(b) mixing a sample of the substance with a solution comprising a dye at a pH between about 4 and about 12, at a temperature between about 0° C. and about 100° C.;
(c) observing any perturbation in the near-infrared or visible absorbance spectrum or fluorescence spectrum of the dye as compared to the spectrum of an otherwise identical and otherwise identically treated solution of the dye that lacks any added homocysteine; and (d) inferring the total homocysteine concentration from a previously-determined correlation between observed perturbations in the spectrum of the dye and total homocysteine concentration;

wherein:

the dye comprises

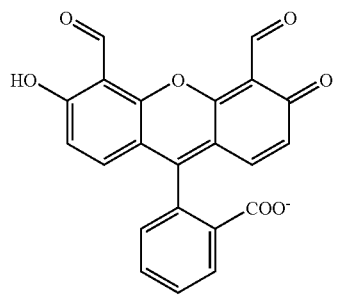

and wherein:

the cysteine-scavenger inhibits any cysteine in the sample from substantially interfering with the determination of the homocysteine concentration.

15. A process as recited in claim 14, wherein the pH is between about 6.5 and about 9.5.

16. A process as recited in claim 14, wherein the solution comprises a solvent selected from the group consisting of water, dimethylformamide, dimethylsulfoxide, acetone, tetrahydrofuran, methanol, ethanol, and acetonitrile.

17. A process as recited in claim 14, wherein said process is conducted in the presence of atmospheric oxygen.

18. A process as recited in claim 14, wherein the substance comprises plasma.

* * * * *